United States Patent
Bruce et al.

(10) Patent No.: US 8,106,193 B2
(45) Date of Patent: Jan. 31, 2012

(54) LUMINOPHORES

(75) Inventors: Duncan W. Bruce, York (GB); Valery Kozhevnikov, Newcastle upon Tyne (GB)

(73) Assignee: University of York, Heslington, York (GB)

( * ) Notice: Subject to any disclaimer, the term of this patent is extended or adjusted under 35 U.S.C. 154(b) by 0 days.

(21) Appl. No.: 12/680,045

(22) PCT Filed: Sep. 29, 2008

(86) PCT No.: PCT/GB2008/003285
§ 371 (c)(1),
(2), (4) Date: Jul. 27, 2010

(87) PCT Pub. No.: WO2009/040551
PCT Pub. Date: Apr. 2, 2009

(65) Prior Publication Data
US 2010/0317851 A1    Dec. 16, 2010

(30) Foreign Application Priority Data
Sep. 28, 2007  (GB) .................................. 0718909.5

(51) Int. Cl.
C07D 403/10    (2006.01)
C07D 401/10    (2006.01)
C07F 15/00     (2006.01)

(52) U.S. Cl. ............ 544/182; 546/4; 546/261; 546/263; 546/266

(58) Field of Classification Search ......................... None
See application file for complete search history.

(56) References Cited

OTHER PUBLICATIONS

Baik et al., Synthesis and photophysical properties of luminescent platinum(II) complexes with terdentate polypyridine ligands: [Pt(bpqb)X] and [Pt(tbbpqpy)X](PF6) (bpqb-H=1,3-bis(4'-phenyl-2'-quinolinyl)benzene; tbbpqpy=4-tert-butyl-1,3-bis(4'-phenyl-2'-quinolinyl)pyridine; X=Cl, CCC6H5, CCC6H4NMe2, CCC6H4NO2), 691(26) J. Organometallic Chem.*
Baik et al., 691(26) J. Organometallic Chem. 5900-5910 (2006).*

* cited by examiner

*Primary Examiner* — Janet Andres
*Assistant Examiner* — Timothy R Rozof
(74) *Attorney, Agent, or Firm* — Choate, Hall & Stewart LLP; Fangli Chen; Paul A. Nuzzi

(57) ABSTRACT

There is described novel organo-platinum luminophores comprising a complex of formula (I). The luminophores have application as the emissive component in organic light emitting diodes.

(I)

7 Claims, 2 Drawing Sheets

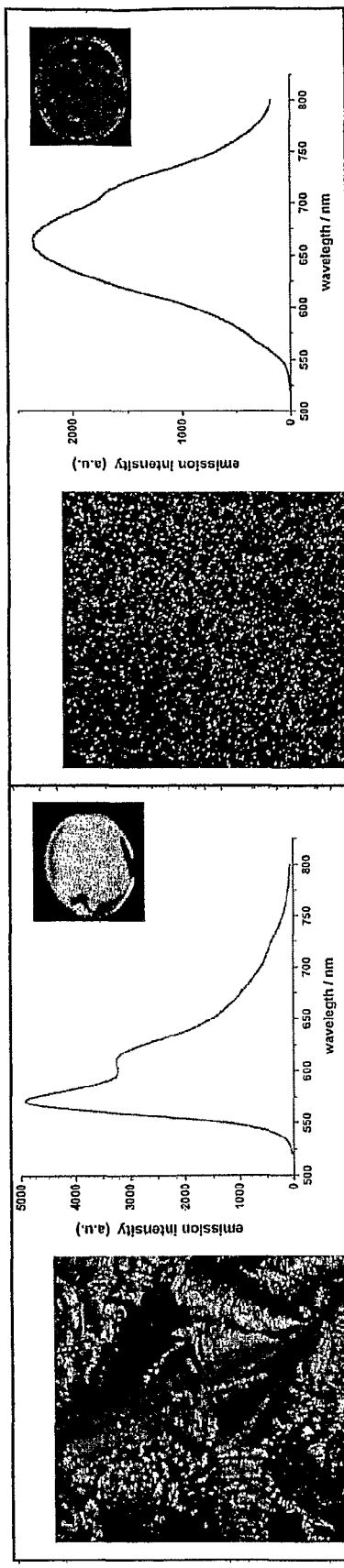
Figure 1 Photomicrographs, emission spectra and samples (inset) of 2-6 at room temperature sandwiched between glass slides: fast cooled from isotropic phase (right) and LC phase *after* texture is fully developed (left).

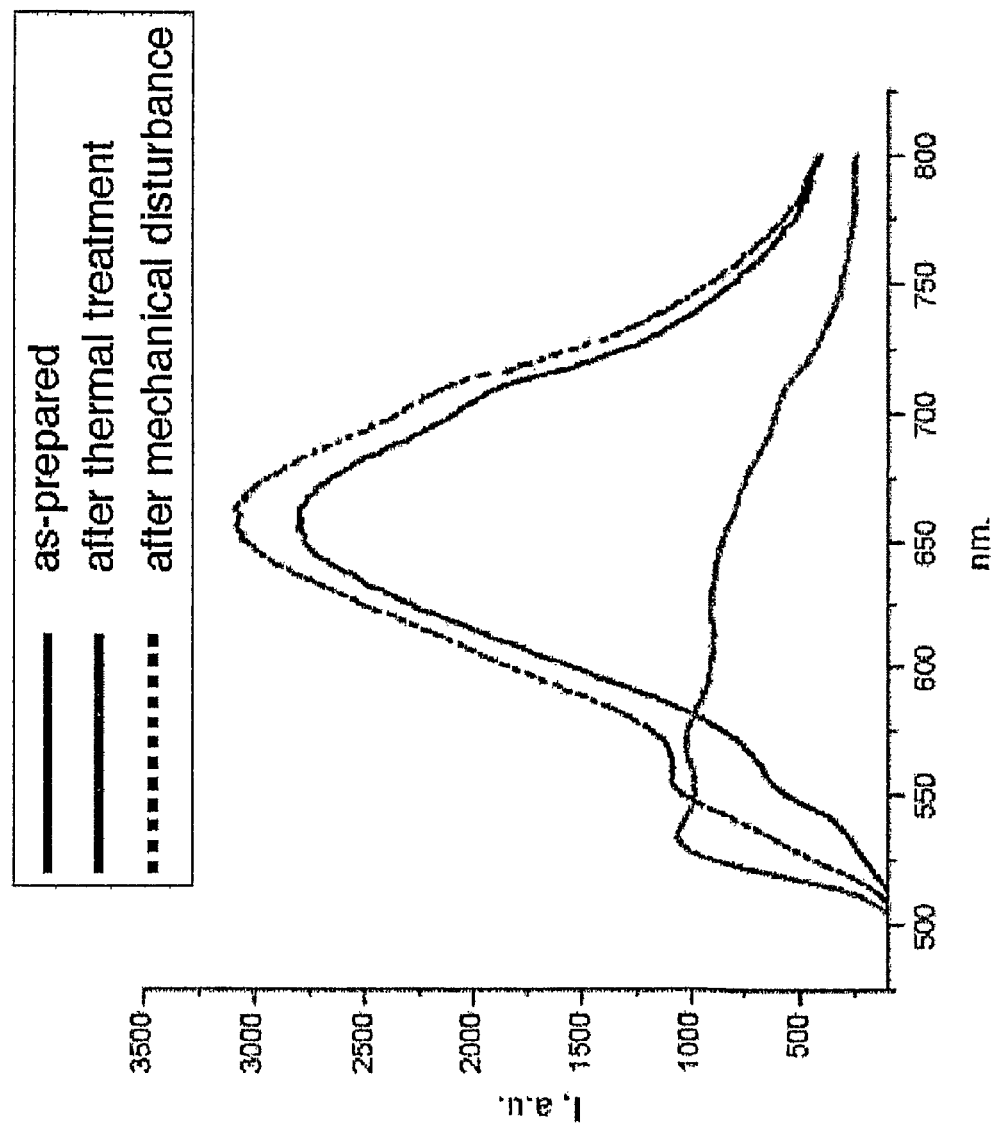
Figure 2  Spin-coated samples of 3-10

LUMINOPHORES

CROSS-REFERENCE TO RELATED APPLICATIONS

This application is a national phase application of International Application No. PCT/GB2008/003285 (PCT Pub. No. WO/2009/040551), filed Sep. 29, 2008, which claims priority to Great Britain Application No. 0718909.5, filed Sep. 28, 2007, the entire contents of both of which are incorporated herein by reference.

FIELD OF THE INVENTION

The present invention relates to novel organo-platinum luminophores with application as the emissive component in organic light emitting diodes, methods of their preparation and their use. More particularly, the invention relates to novel liquid crystals which are also light emitting materials. Thus, the invention also relates to materials comprising such liquid crystals and the use of such materials in, for example, display devices. The invention also relates to the ligands use in such organo-platinum luminophores.

BACKGROUND TO THE INVENTION

So-called Organic Light-Emitting Diodes (OLEDs) have been the focus of substantial recent attention. OLEDs are widely used in a new generation of low-power, flat-panel (and flexible) displays. Among the advantages offered by OLEDs is the possibility for preparation of very flexible displays in novel formats such as conformable panels or coatings for textiles and also the fact that backlighting is not required, so reducing energy consumption.

Whilst much of the effort has been directed towards purely organic systems (particularly in relation to light-emitting polymers), more recently metal-organic systems employing, in particular, third-row transition elements have attracted interest for use in OLED displays.[i] The reason for this lies in the short lifetime of the triplet excited states which are produced when charge is injected into the device. Triplet states of organic materials which are produced in OLED devices are typically long-lived as emission is a spin-forbidden process and so emission is from only one (singlet) of four (singlet plus three triplet) excited states produced. However, the presence of a heavy transition element facilitates efficient spin-orbit coupling, shortening the lifetime of the triplet states and allowing emission from all four excited states produced. In functional terms, this means that OLEDS fabricated from metal complexes could in principle emit up to four times as much light as conventional OLEDs.

Known metal-organic luminophores that emit from triplet states are based on, for example:
- octahedral complexes of iridium(III) containing two N—C chelates;
- square-planar complexes of platinum(II) bound to a single N—C—N chelate; and
- square-planar complexes of platinum(II) bound to an N—C chelate.

In general, existing OLED materials are vacuum deposited or spin coated as layers into devices and, as such, are present in an amorphous state, i.e. having no long range structural order. By contrast, liquid crystals do have long range structural order, when arranged in mesophases. An attractive and central feature of liquid crystal mesophases is that the organisation of the molecules therein results in attendant anisotropy of the physical properties.

Although OLED displays based on emissive metal complexes are likely to be energy efficient compared to existing technology, incorporating long range order and anisotropic properties into thin films of materials used to make metal-organic OLED displays could make a significant further increase in their energy efficiency.

Therefore, the combination of liquid crystal properties and light-emitting properties in a single compound/complex would be very desirable. For example, emission from aligned layers of calamitic (rod-like) liquid crystals leads to polarised emission. Emission of polarized light from a display reduces scattering and makes the display appear brighter. Alternatively, materials capable of forming columnar phases may lead to greatly enhanced charge carrier mobilities[ii] compared to amorphous materials. This would reduce the amount of electricity needed to power a display.

These properties can be used to improve the quality of the display and to reduce the power needed for the display to work, thus extending the battery life of a portable device such as a mobile phone or a laptop computer. Other advantages of incorporating liquid crystalline properties into a metal-organic OLED display may be envisaged.

We have now surprisingly found a group of novel organo-platinum complexes which possess the property of being phosphorescent and, in some cases, are liquid crystals in which the luminescence properties in the mesophase can be controlled to be quite different from those of the amorphous material.

DESCRIPTION OF THE INVENTION

The present invention is based on the discovery of novel materials which are luminescent and more particularly materials which combine the properties of both liquid crystals and luminescence, e.g. phosphorescent, metal-organic complexes.

Thus, according to a first aspect of the invention we provide a metal-ligand complex comprising a complex of formula I:

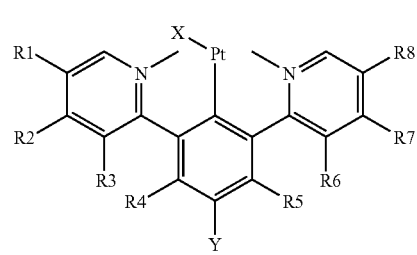

in which $R^1$ and $R^8$, which may be the same or different, are each a group of formula II;

$$—Z—R^{12} \quad\quad\quad II$$

Z is a sigma-bond, —C═C—, —C≡C—, —$(CH_2)_x$—, —COO—, —OC(═O)—, —CH═N—, —N═CH—, —C(═O)NH—, —NHC(═O)—, —$(CH_2)_q$O—, —O—$(CH_2)_w$— or —OC(═O)$X^1R^{14}$—;

$R^{12}$ is alkyl C1 to 18 or a group of formula VIII;

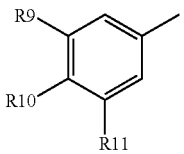

VIII $R^2$, $R^3$, $R^6$ and $R^7$, which may be the same or different, are each hydrogen or together the pair of $R^2$ and $R^3$ and/or $R^6$ and $R^7$, form a —$(CH_2)_m$— ring;

$R^4$ and $R^5$, which may be the same or different, are each hydrogen or halogen;

X is an anionic function which may be a phenate, a thiolate, an acetylide, a phenyl, an alkyl, vinyl, each of which may optionally be substituted by alkyl C1 to 30 or X is a halide;

$X^1$ is C5 or C6 cycloalkyl;

Y is hydrogen, hydroxy, halogen, alkyl C1 to 6, haloalkyl C1 to 6, alkoxy C1 to 6, —$COOR^{13}$, cyano or isothiocyanate;

$R^9$ and $R^{11}$, which may be the same or different, are each hydrogen or —$OC_nH_{2n+1}$;

$R^{10}$ is hydrogen, —$OC_yH_{2y+1}$ $R^{13}$ is hydrogen or alkyl C1 to 18;

$R^{14}$ is alkyl C1 to 12;

m is an integer from 3 to 8;

n and y, which may be the same or different, are each an integer from 1 to 30; and x, q and w, which may be the same or different, are each an integer from 1 to 12.

It will be understood by the person skilled in the art that the platinum in the complex of formula I is $Pt^{II}$.

In one aspect of the invention each of $R^2$, $R^3$, $R^6$ and $R^7$ is hydrogen. In a further aspect of the invention when a pair of $R^2$ and $R^3$ or $R^6$ and $R^7$ forms a —$(CH_2)_m$— ring, m is 3. In a yet further aspect of the invention the pair $R^2$ and $R^3$; and the pair $R^6$ and $R^7$ forms a —$(CH_2)_3$— ring.

$R^4$ and $R^5$ are each preferably F.

X is preferably Cl.

Each of $R^9$, $R^{10}$ and $R^{11}$ is preferably —$OC_nH_{2n+1}$. In a further aspect of the invention $R^9$ and $R^{11}$ are the same and $R^{10}$ is different. In a further aspect of the invention $R^9$ and $R^{10}$ are the same and $R^{11}$ is different. In a further aspect of the invention $R^{10}$ and $R^{11}$ are the same and $R^9$ is different.

In one aspect of the invention n is from 5 to 15, alternatively from 9 to 14 and alternatively 12.

Although the present invention specifically relates to the metal complexes of formula I as hereinbefore described, the organic moiety is novel per se. Therefore, according to a further aspect of the invention we provide a compound of formula III,

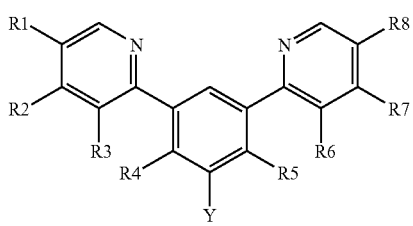

III in which in $R^1$, $R^2$, $R^3$, $R^4$, $R^5$, $R^6$, $R^7$, $R^8$, $R^9$, $R^{10}$, $R^{11}$, Y, m and n are each as hereinbefore described, provided that one or both of $R^1$ and $R^8$ is not hydrogen.

According to a yet further aspect of the present invention we provide a method of manufacturing a complex of formula I which comprises reacting a compound of formula III, as hereinbefore described with a $Pt^{II}$ salt.

Although a variety of $Pt^{II}$ salts may be used, a preferred salt is a $Pt^{II}$ halide, such as the chloride. Especially preferred is the co-salt of a Group 1 metal, such as $K_2[PtCl_4]$.

According a yet further aspect of the invention we provide a process for the manufacture of a compound of formula III which comprises alkylating a compound of formula IV;

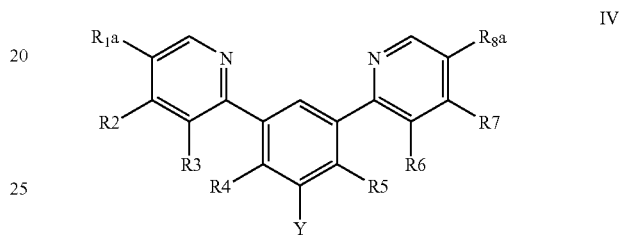

IV in which in $R^2$, $R^3$, $R^4$, $R^5$, $R^6$, $R^7$ and Y are each as hereinbefore described, and $R^{1a}$ and $R^{8a}$, which may be the same or different, are each a group of formula V;

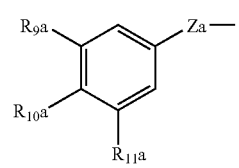

V in which $R^{9a}$, $R^{10a}$ and $R^{11a}$, which may be the same or different, are each hydrogen or —OH, provided that at least one of $R^{9a}$, $R^{10a}$ and $R^{11a}$ is not hydrogen; and Za is a bond.

A compound of formula IV may be prepared by reducing a compound of formula VI;

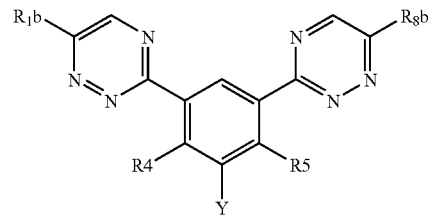

VI in which in $R^4$, $R^5$ and Y are each as hereinbefore described, and $R^{1b}$ and $R^{8b}$, which may be the same or different, are each a group of formula VII;

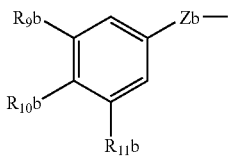

VII in which $R^{9b}$, $R^{10b}$ and $R^{11b}$, which may be the same or different, are each hydrogen or alkoxy C1 to 12; and Zb is a bond.

According to a further aspect of the invention we provide a material comprising a phosphorescent organo-platinum liquid crystal as hereinbefore described. Thus, such a material is advantageous in that, inter alia, it is a luminophore and may also be a liquid crystal.

Thus, we also provide the use of the material as hereinbefore described in the manufacture of an electronic device. The material is advantageous in that, inter alia, such electronic devices may be more energy-efficient and/or brighter than conventionally know devices.

It is within the scope of the present invention to provide a material comprising the organo-platinum luminophore as hereinbefore described in combination with one or more known liquid crystals.

The $Pt^{II}$ complexes of 1,3-di(pyridin-2-yl)benzene may have an excited-state lifetime of some 7.2 microseconds and a luminescence quantum yield of 0.6.

The invention will now be described by way of example only and with reference to the accompanying figures in which FIG. 1(a) shows a photomicrograph of the columnar mesophase in a glassy state;

FIG. 1(b) shows the photomicrograph obtained when the same complex is cooled rapidly directly from the isotropic melt; and FIG. 2 shows spectra from samples of spin coated onto a glass substrate.

In a further aspect of the invention we also provide each of the complexes and the ligands related thereto which are described herein in the following examples, 1 to 23.

EXAMPLES

In these examples are described the synthesis and properties of luminescent platinum (II) complexes, which show columnar liquid crystal mesophases.

The ligands are based on the 3,5-bis(2'-pyridyl)benzene moiety and are prepared using a cyclisation/retro Diels-Alder pathway as shown in the scheme below. Full details are given in the experimental section.

Specifically, considering the final complex for X=Cl and n=12, we find the following phase behaviour:

Cr.95.Col.151.I

Further, photochemical measurements show that the complex emits in solution in $CH_2Cl_2$ and in the solid state. Luminescent properties are similar to highly luminescent Pt complexes reported by Williams[iii].

The complexes of the invention may be prepared using the following general reaction scheme:

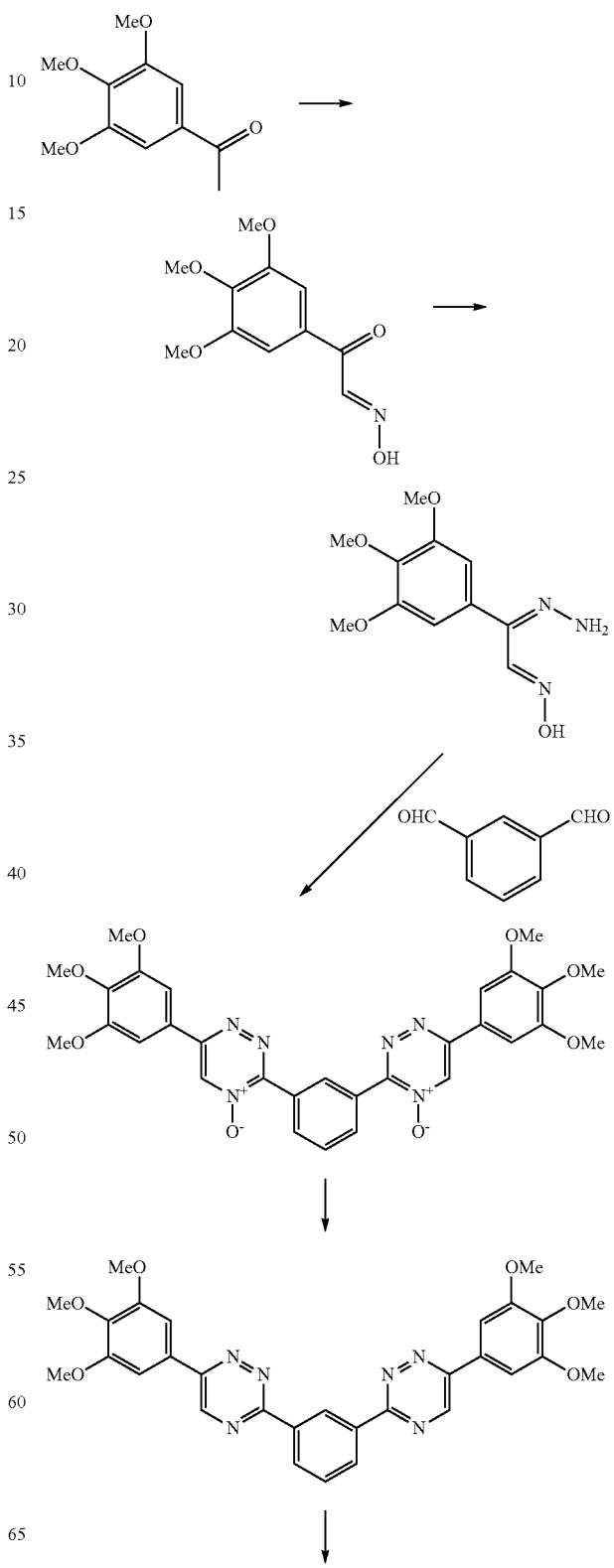

-continued

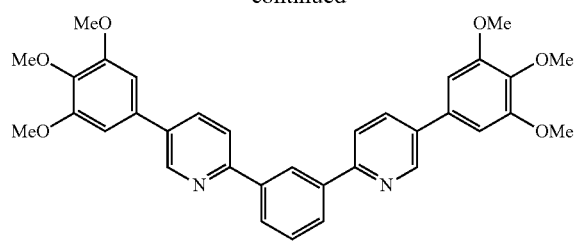

↓

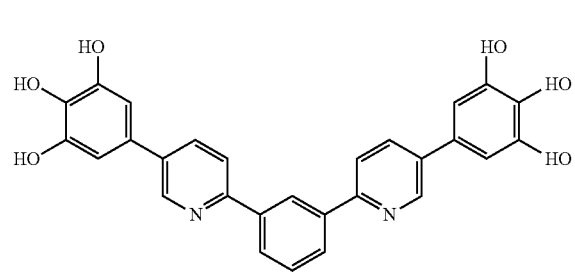

↓

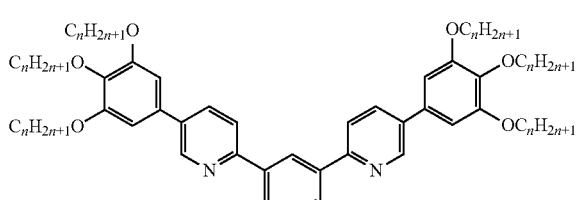

↓

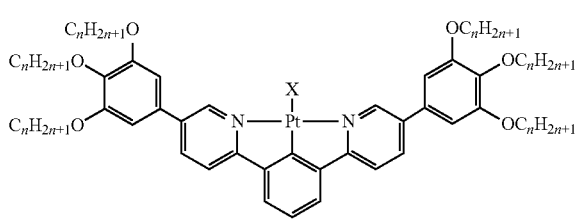

EXPERIMENTAL

Example 1

1,3-[5-(3,4,5-tri{hexadecyloxy}phenyl)pyridine-2-yl]-benzene (n=16)

1.1 1-(3,4,5-trimethoxyphenyl)-1,2-ethanedione-2-oxime[iv]

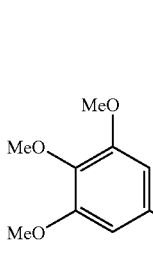 →

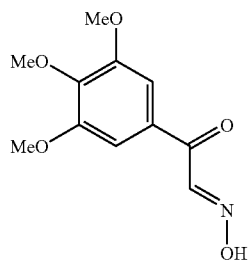

To a mixture of 3,4,5-trimethoxyacetophenone (50 g, 0.24 mol), ethanol (100 cm$^3$) and isopropyl nitrite (42 cm$^3$, 0.4 mol) was added to a solution of sodium ethoxide prepared by addition of sodium (6.9 g, 0.3 mol) to absolute ethanol (300 cm$^3$). The reaction mixture was stirred at room temperature for 20 h. The precipitated solid was separated by filtration, washed with ethanol (50 cm$^3$) and diethyl ether (100 cm$^3$), dried in vacuum and then dissolved in water (300 cm$^3$). To this solution an acetic acid (14 cm$^3$, 0.24 mol) was added, which caused a precipitation. The solid was separated by filtration, washed with water and dried to give the title compound. Yield 31 g (54%). Mp 87-89° C.; $\delta_H$ (CDCl$_3$): 3.87 (s, 6H), 3.91 (s, 3H), 7.33 (s, 2H), 8.12 (s, 1H).

1.2 1-(3,4,5-trimethoxyphenyl)-1,2-ethanedione-1-hydrazone 2-oxime[Y]

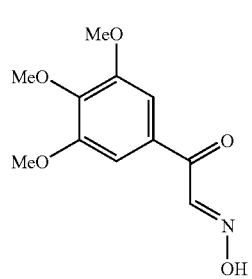

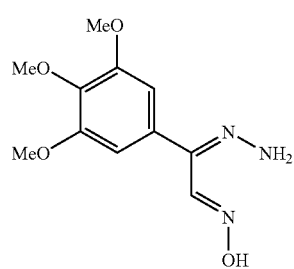

Hydrazine hydrate (10 g, 0.2 mol) was added to a solution of 1-(3,4,5-trimethoxyphenyl)-1,2-ethanedione 2-oxime (24 g, 0.1 mol) in ethanol (100 ml) and the reaction mixture was stirred at room temperature for 5 hours. Water was added; the precipitated solid was filtered off, washed with water and dried. Yield 10.8 g (43%). $\delta_H$ (DMSO-$d_6$): 3.65 (s, 3H), 3.81 (s, 6H), 6.81 (s, 2H), 8.32 (s, 1H), 8.94 (s, 2H), 11.6 (s, 1H).

1.3 1,3-[5-(3,4,5-trimethoxyphenyl)-1,2,4-triazine-4-oxide-2-yl]-benzene

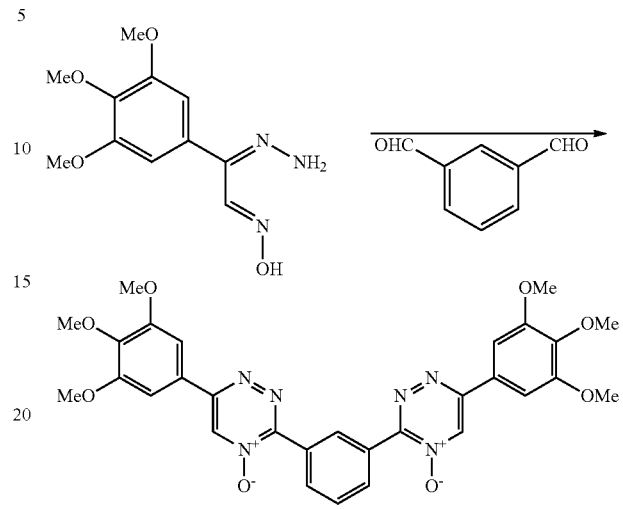

A solution of isophthalic dicarboxaldehyde (4.02 g, 30 mmol) in acetic acid (50 cm³) was added to a stirred solution of 1-(3,4,5-trimethoxyphenyl)-1,2-ethanedione 1-hydrazone-2-oxime (15.2 g, 60 mmol) in acetic acid (100 cm³) and the reaction mixture was stirred at 50° C. for 6 hours. The reaction mixture was allowed to cool to room temperature and Pb$_3$O$_4$ (41.1 g, 60 mmol) was added in portions over a period of 2 hours. The reaction mixture was stirred at room temperature for 4 hours. Precipitated solid was filtered off and washed with acetic acid and recrystallised from acetic acid to give titled compound. Yield 18 g, 56%; $\delta_H$ (CDCl$_3$): 3.97 (s, 3H), 4.00 (s, 6H), 7.32 (s, 2H), 7.76 (t, ³$J_{HH}$ 7.7 Hz, 1H), 8.64 (s, 2H), 8.65 (dd, ³$J_{HH}$ 7.7 Hz, ⁴$J_{HH}$ 1.8 Hz, 2H), 9.58 (t, ⁴$J_{HH}$ 1.8 Hz, 1H)

1.4 1,3-[5-(3,4,5-trimethoxyphenyl)-1,2,4-triazine-2-yl]-benzene

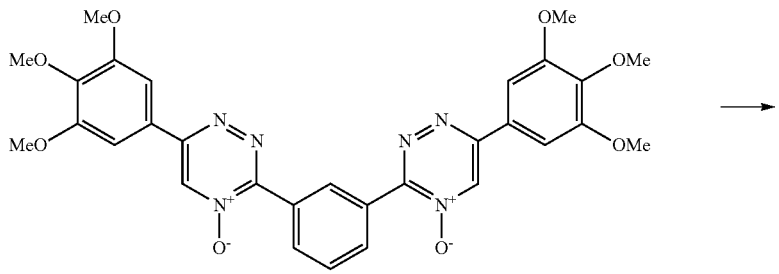

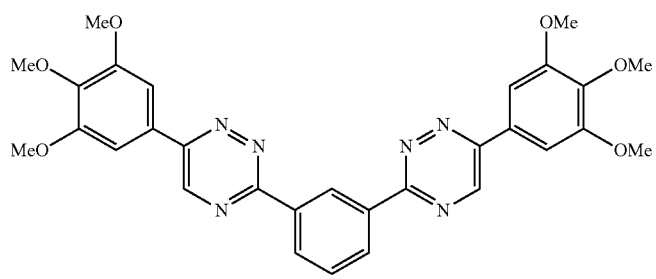

A suspension of 1,3-[5-(3,4,5-trimethoxyphenyl)-1,2,4-triazine-4-oxide-2-yl]-benzene (15 g, 25 mmol) in triethylphosphite (50 cm³) was heated under reflux for 12 h. The reaction mixture was allowed to cool room temperature; solid was filtered off and washed with ethanol to give required compound. Yield 13.9 g, 98%; $\delta_H$ (CDCl$_3$): 3.95 (s, 3H), 4.04 (s, 6H), 7.43 (s, 2H), 7.75 (t, $^3J_{HH}$ 7.7 Hz, 1H), 8.79 (dd, $^3J_{HH}$ 7.7 Hz, $^4J_{HH}$ 1.8 Hz, 2H), 9.07 (s, 2H), 9.76 (t, $^4J_{HH}$ 1.8 Hz, 1H)

1.5 1,3-[5-(3,4,5-trimethoxyphenyl)pyridine-2-yl]-benzene

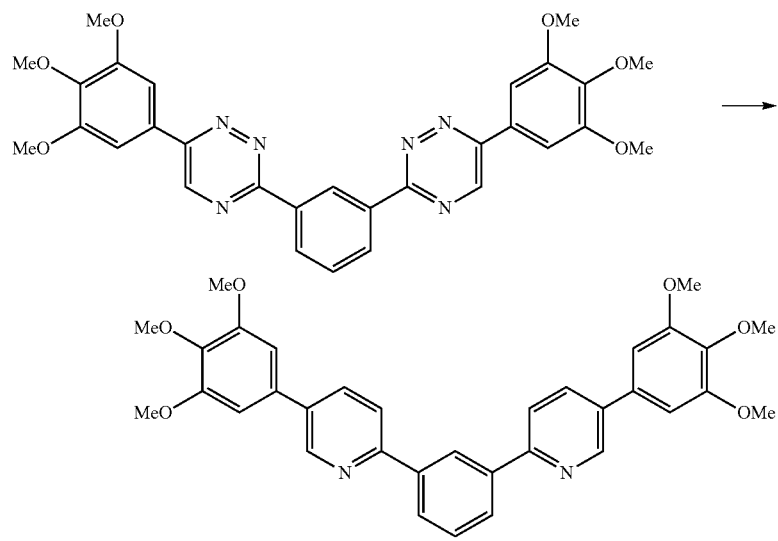

An autoclave equipped with stirring bar was charged with the 1,3-[5-(3,4,5-trimethoxyphenyl)-1,2,4-triazine-2-yl]-benzene (3 g, 5.3 mmol), xylene (50 cm³) and norbornadiene (5.4 cm³, 53 mmol). The autoclave was sealed, placed in oil bath and heated at 200° C. (bath) for 24 h. The reaction mixture was filtered through a small pad of silica gel while hot, the silica gel was washed with DCM until no product present in the filtrate (which is checked by TLC). All filtrates were combined and the solvent was removed under reduced pressure. The residue was triturated with ethanol, the formed solid was filtered off and washed with ethanol to give the desired product. Yield 2.6 g, 87%; $\delta_H$ (CDCl$_3$): 3.91 (s, 3H), 3.98 (s, 6H), 6.82 (s, 2H), 7.63 (t, $^3J_{HH}$ 7.7 Hz, 1H), 7.94 (br. s, 4H), 8.11 (dd, $^3J_{HH}$ 7.7 Hz, $^4J_{HH}$ 1.8 Hz, 2H), 8.74 (t, $^4J_{HH}$ 1.8 Hz, 1H), 8.93 (br. s, 2H).

1.6 1,3-[5-(3,4,5-trihydroxyphenyl)pyridine-2-yl]-benzene

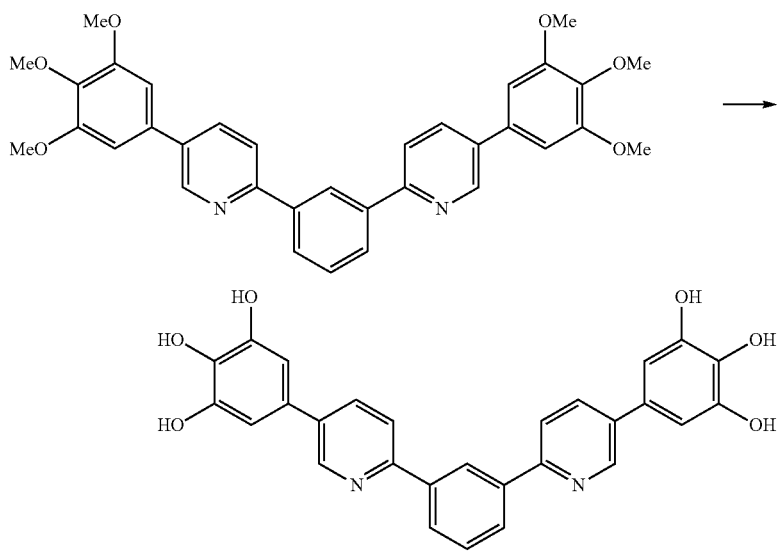

The mixture of anhydrous pyridine hydrochloride[vi] (35.0 g) and 1,3-[5-(3,4,5-trimethoxyphenyl)pyridine-2-yl]-benzene (7 g, 12.4 mmol) was stirred at 200° C. for 12 h. The hot solution was quenched carefully with water (50 cm$^3$). The resulting precipitate was filtered off, washed thoroughly with water, hot acetone, and dried in vacuum to yield the desired product (5.3 g, 89%). $\delta_H$ (DMSO-d$_6$)=6.74 (s, 4H), 7.73 (t, $^3J_{HH}$ 7.7 Hz, 1H), 8.21 (br. d, $^3J_{HH}$ 7.7 Hz, 2H), 8.26 (br. s, 4H), 8.81 (br. s, 1H), 8.87 (br. s, 2H).

1.7 1,3-[5-(3,4,5-tri{hexadecyloxy}phenyl)pyridine-2-yl]-benzene (n=16)

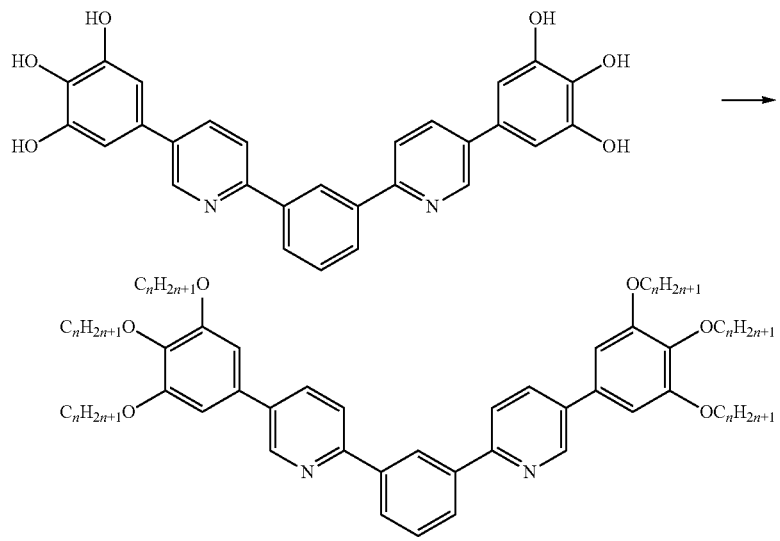

A mixture of 1,3-[5-(3,4,5-trihydroxyphenyl)pyridine-2-yl]-benzene (mg, mmol), potassium carbonate (207 mg, 1.5 mmol), 1-bromoalkane (0.51 mmol) and DMF (10 cm$^3$) was stirred at 100° C. for 12 hours. The solvent was removed under reduced pressure; the product was purified by column chromatography (silica gel, DCM/petrol ether/ethyl acetate 10/10/1) to give the required product. Yields were in the range of 65-85%.

Analytical data for compound of formula 1.7: —OC$_{16}$H$_{33}$ substitution $\delta_H$ (CDCl$_3$): 0.81 (m, 18H), 1.20 (m, 144H), 1.43 (m, 12H), 1.5 (m, 12H), 3.94 (t, $^3J_{HH}$ 6.7 Hz, 4H), 4.00 (t, $^3J_{HH}$ 6.7 Hz, 8H), 6.73 (s, 2H), 7.54 (t, $^3J_{HH}$ 7.7 Hz, 1H), 7.85 (m, 4H), 8.07 (dd, $^3J_{HH}$ 7.7 Hz, $^4J_{HH}$ 1.8 Hz, 2H), 8.64 (t, $^4J_{HH}$ 1.8 Hz, 1H), 8.85 (d, $^4J_{HH}$ 2.1 Hz, 2H).

Example 2

Preparation of Platinum(II) Complexes [PtClL″]

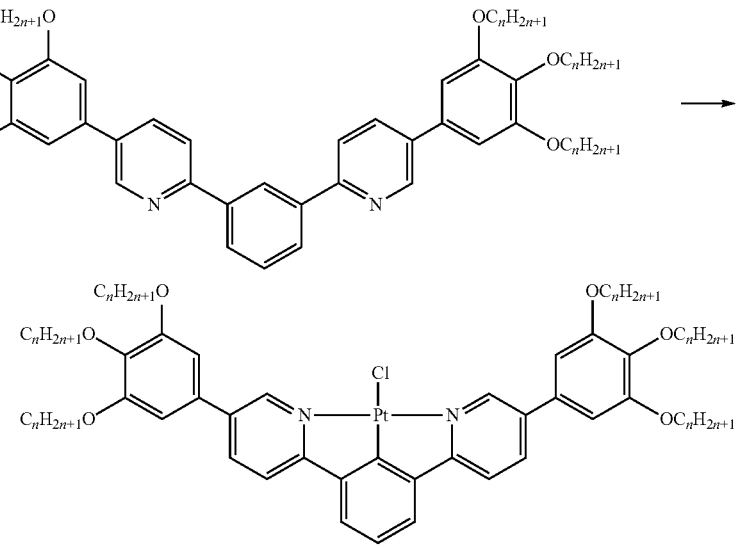

To stirred solution of the ligand HL" (typically 0.2 mmol) in acetic acid (50 cm³) at 100° C. was added a solution of K₂[PtCl₄] in water (1 cm³) and the reaction mixture was heated under reflux for 24 h under nitrogen atmosphere. The solvent was removed in vacuum by rotary evaporation. The product was purified by column chromatography (silica gel, DCM, Rf approx. 0.8) to give the required product. Yields were in the range of 45-60%.

Analytical data for [PtClL$^{16}$]

Yield 67%, $\delta_H$ (CDCl₃): 0.85 (m, 18H), 1.25 (m, 144H), 1.45 (m, 12H), 1.8 (m, 12H), 3.99 (t, $^3J_{HH}$ 6.7 Hz, 4H), 4.04 (t, $^3J_{HH}$ 6.7 Hz, 8H), 6.77 (s, 4H), 7.25 (t, $^3J_{HH}$ 7.7 Hz, 1H), 7.45 (d, $^3J_{HH}$ 7.7 Hz, 2H), 7.68 (d, $^3J_{HH}$ 8.5 Hz, 2H), 8.05 (dd, $^3J_{HH}$ 8.5 Hz, $^4J_{HH}$ 2.2 Hz, 2H), 9.59 (d, 1H, $^3J_{HH}$ 2.2 Hz, $^3J_{HPt}$ 37.4 Hz).

Examples 3 to 13

The following compounds were prepared using analogous methods.

Example 3

Example 4

Example 5

Example 6

Example 3

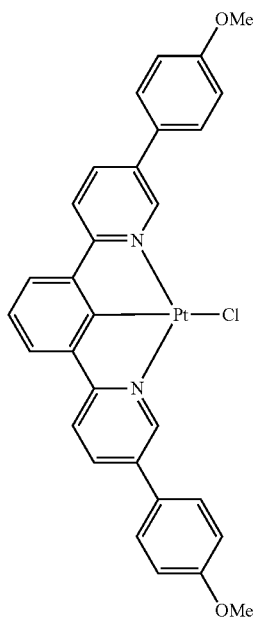

Example 4

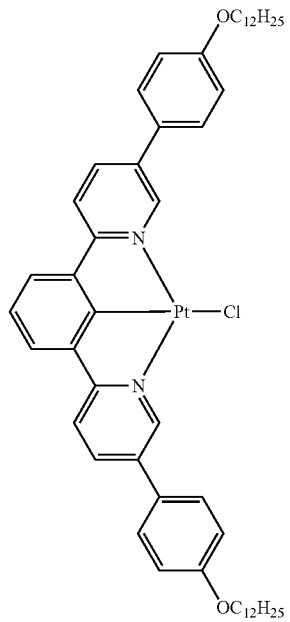

Example 5

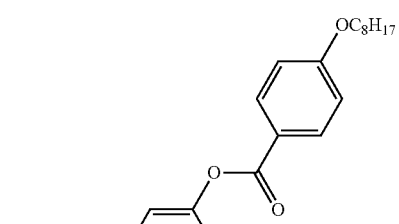

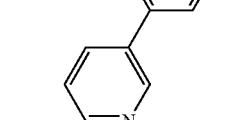

Eample 6
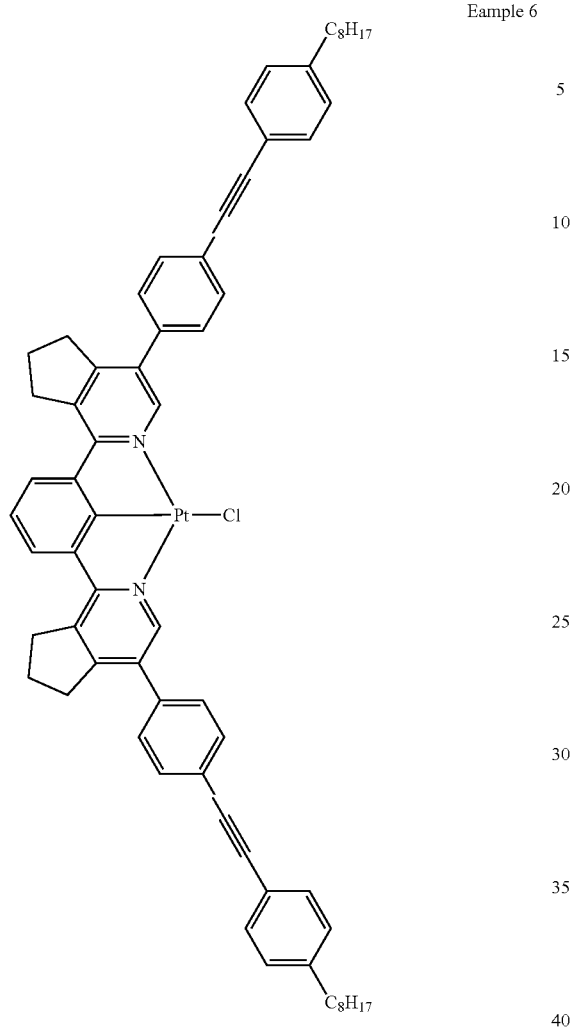
Example 7
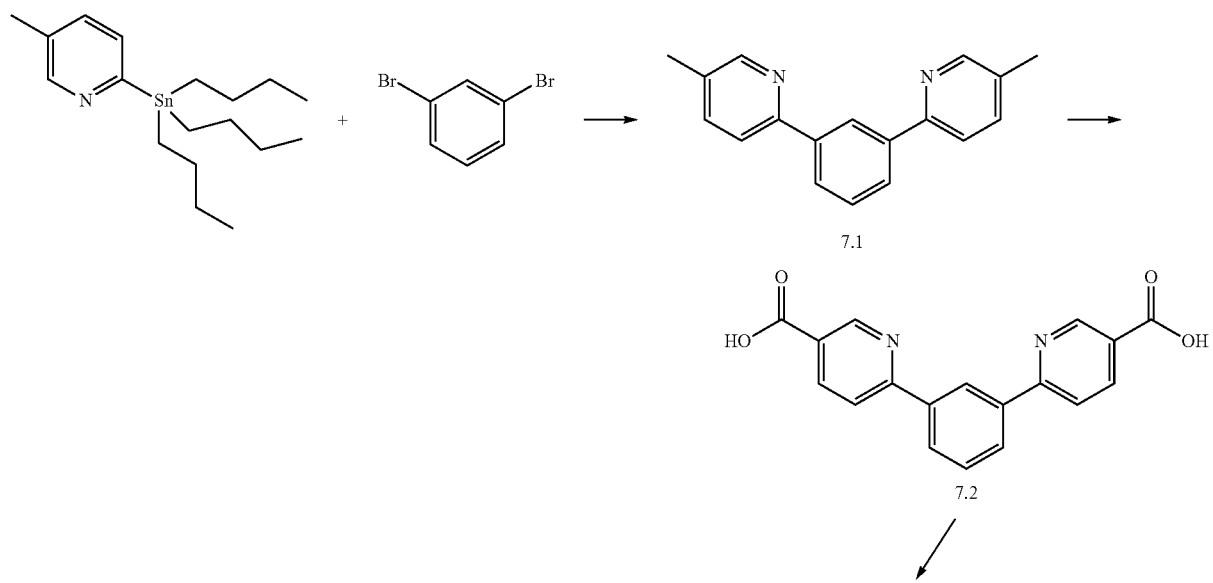
7.1
7.2

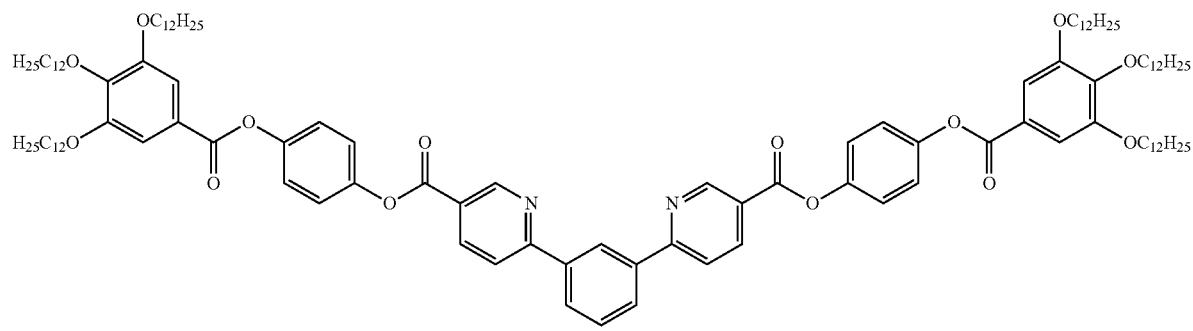

7.3

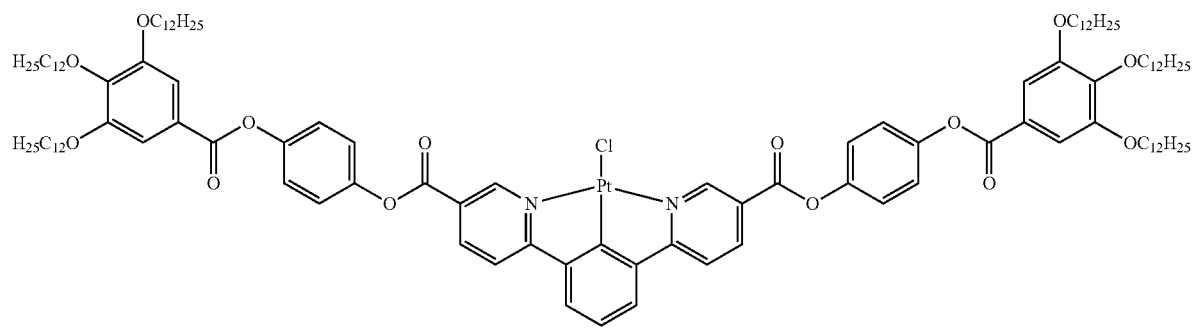

7.4

7.1 1,3-di(5-methyl-2-pyridyl)benzene

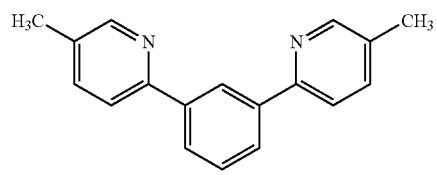

7.2 1,3-di(5-carboxy-2-pyridyl)benzene

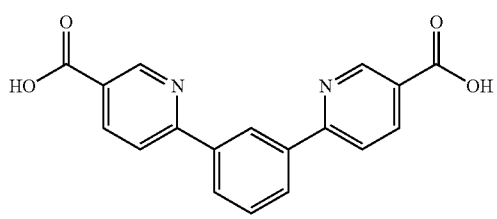

A mixture of 1,3-dibromobenzene (1.88 g, 8 mmol), 5-methyl-2-tri-n-butylstannylpyridine (7.18 g, 18.8 mmol), lithium chloride (28 g, 0.67 mol), bis(triphenylphosphine) palladium dichloride (360 mg, 0.5 mmol) and toluene (150 cm³) was degassed by bubbling argon through the mixture for 15 minutes. The reaction mixture was heated under reflux for 24 h. The mixture was then allowed to cool to room temperature and was filtered through small pad of silica gel, which was then washed with ethyl acetate. The filtrate was evaporated to dryness and the product was purified by column chromatography (silica gel, hexane/ethyl acetate, 1/1) to give the title product as a colourless solid. Yield 728 mg, 35%. $\delta_H$ (270 MHz; CDCl₃): 2.36 (6H, s, 2×CH₃), 7.54 (1H, t, J 8.0, 5-H), 7.56 (2H, dd, J 8.2 and 2.1, 2×py 4-H), 7.72 (2H, d, J 8.2, 2×py 3-H), 7.99 (2H, dd, J 8.0 and 1.8, 4-H, 6-H), 8.52 (2H, d, J 2.1, 2×py 6-H), 8.54 (1H, t, J 1.8, 2-H).

1,3-Di(5-methyl-2-pyridyl)benzene (3 g, 11.5 mmol) was dissolved in pyridine (50 cm³). The solution was diluted with water (100 cm³) and heated to reflux. To this solution potassium permanganate (21.9 g, 138 mmol) was cautiously added in 3 g portions over a period of 6 hours at vigorous stirring. During this time the reaction mixture was heated under reflux. The mixture was filtered the solid on the filter was washed with hot water. Combined filtrates was neutralised by addition of 2M hydrochloric acid. Precipitated solid was filtered off, washed with water and recrystallised from DMF to give the titled product. Yield 2.1 g, 57%. $\delta_H$ (270 MHz; DMS)-d₆): 7.70 (1H, t, J 8.0, 5-H), 8.25 (2H, d, J 8.2 2×py 3-H), 8.31 (2H, dd, J 8.0 and 1.8, 4-H, 6-H), 8.37 (2H, dd, J 8.2 and 2.1, 2×py 4-H), 8.96 (1H, t, J 1.8, 2-H), 9.19 (2H, d, J 2.1, 2×py 6-H).

7.3 Ligand

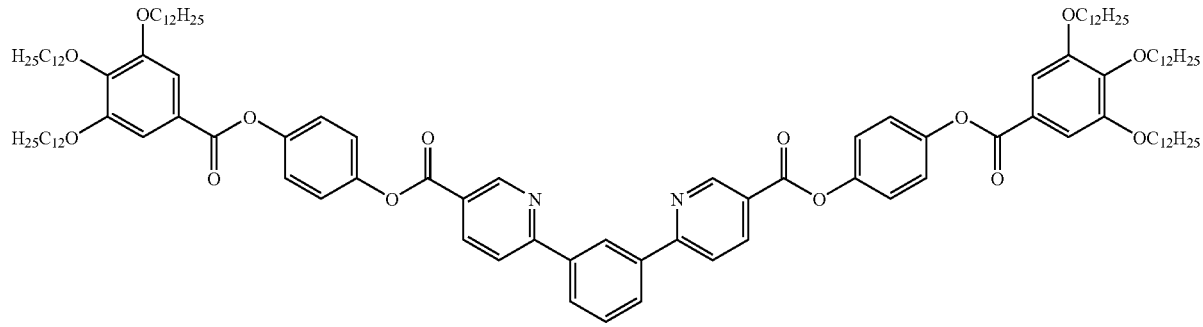

A mixture of 1,3-di(5-carboxy-2-pyridyl)benzene 7.2 (320 mg, 1 mmol) and thionyl chloride (3 cm$^3$) was heated under reflux for 12 hours. All volatile components were removed in vacuum and the residue was dissolved in dry DCM (10 cm$^3$) and added to a solution of the phenol (1674 mg, 2.2 mmol), DMAP (70 mg, 0.57 mmol, cat) and TEA (3 cm$^3$) in dry DCM (20 cm$^3$). The reaction mixture was heated under reflux for 24 hours. The solvent was removed by rotary evaporation under reduced pressure. The residue was suspended in acetone (10 cm$^3$), the solid was separated by filtration and washed subsequently with acetone (3 cm$^3$), water (20 cm$^3$), acetone (3 cm$^3$). The product was finally purified by recrystallisation from acetone. Yield 1024 mg, 57%. $\delta_H$ (400 MHz; CDCl$_3$): 0.81 (18H, t, J 7.4, 6×CH$_3$), 1.14-1.32 (96H, m), 1.42 (12H, q, J 8.0), 1.70 (4H, q, J 7.8), 1.77 (8H, q, J 7.8), 3.99 (8H, t, J 5.1, 4×OCH$_2$), 4.00 (4H, t, J 5.1, 2×OCH$_2$), 7.22 (4H, AA'XX', J 9.1), 7.27 (4H, AA'XX', J 9.1), 7.32 (4H, s, Ar), 7.92 (2H, br, d, J 8.2 2×py 3-H), 8.61 (2H, dd, J 8.2 and 2.1, 2×py 4-H), 9.80 (2H, dd, J 2.2, and 0.9, 2×py 6-H).

7.4 Platinum (II) Complex

A mixture of the ligand 7.3 (181 mg, 0.1 mmol) and acetic acid (50 cm$^3$) was degassed by bubbling Ar through the mixture for 10 min. Dichlorobis(benzonitrile)-platinum (II) (48 mg, 0.1 mmol) was added and the reaction mixture was heated under reflux for 3 days. The solvent was removed under reduced pressure. DMSO was added and the mixture was heated under reflux for 5 minutes. The solvent was removed in vacuum, and the product was purified by column chromatography(silica gel, DCM) to give the complex. Yield 8 mg, 4%. $\delta_H$ (400 MHz; CDCl$_3$): 0.81 (18H, t, J 7.4), 1.14-1.32 (96H, m), 1.42 (12H, m), 1.70 (4H, q, J 7.8), 1.77 (8H, q, J 7.8), 3.98 (8H, t, J 5.1), 4.00 (4H, t, J 5.1), 7.19 (1H, t, J 8.0), 7.20 (4H, AA'XX', J 9.1), 7.26 (4H, AA'XX', J 9.1), 7.34 (4H, s), 7.58 (2H, d, J 8.0), 7.81 (2H, br, d, J 8.2), 8.64 (2H, dd, J 8.2 and 2.1), 10.04 (2H, d, J 2.1).

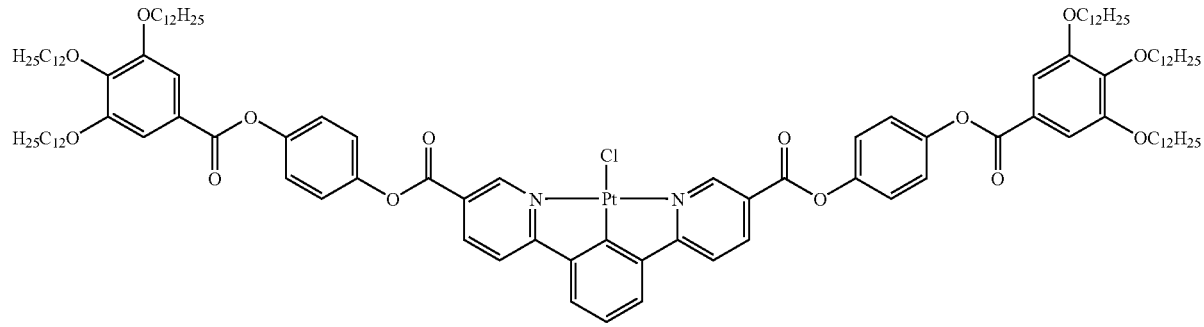

Examples 8 to 11
The following compounds were prepared by analogous methods to Example 7.
Example 8
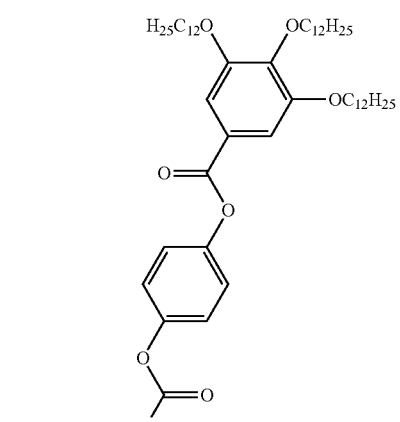
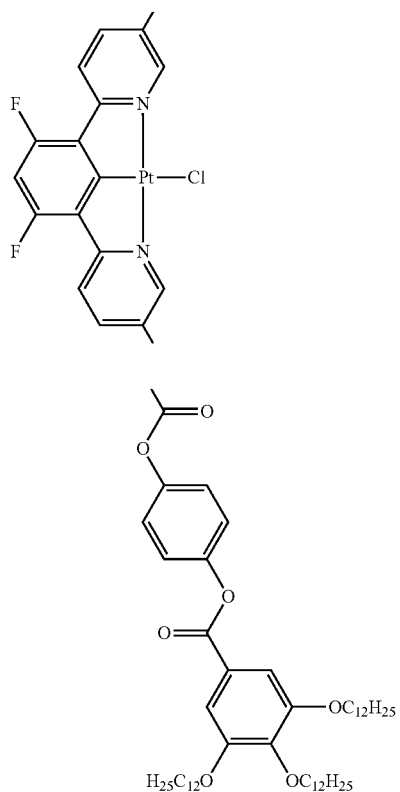
Example 9
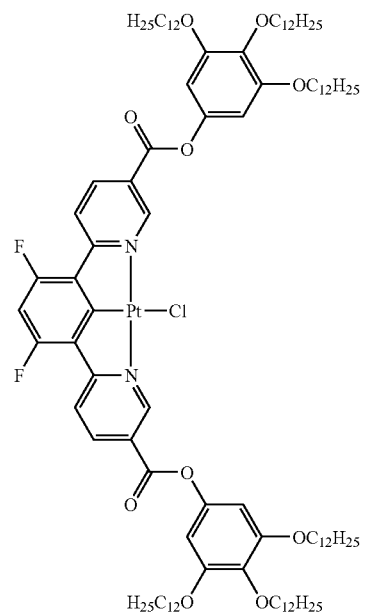
Example 10
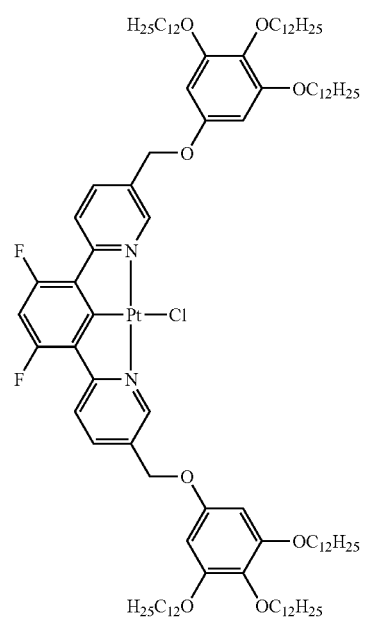

Example 11
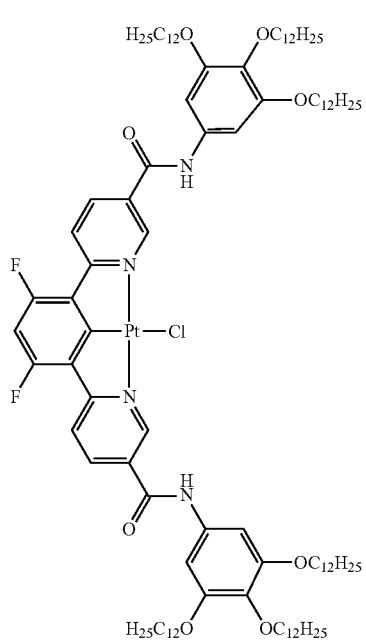
Example 12
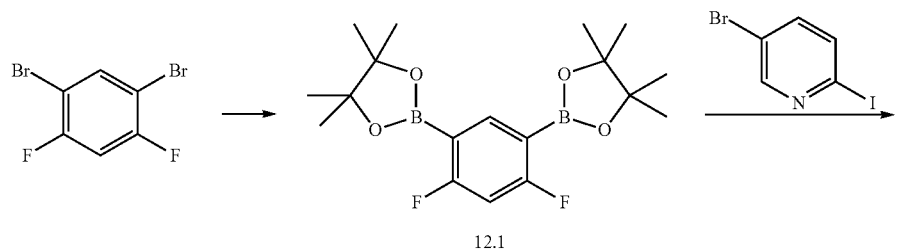
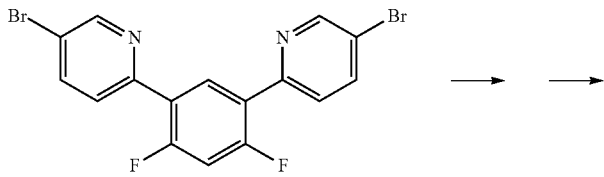
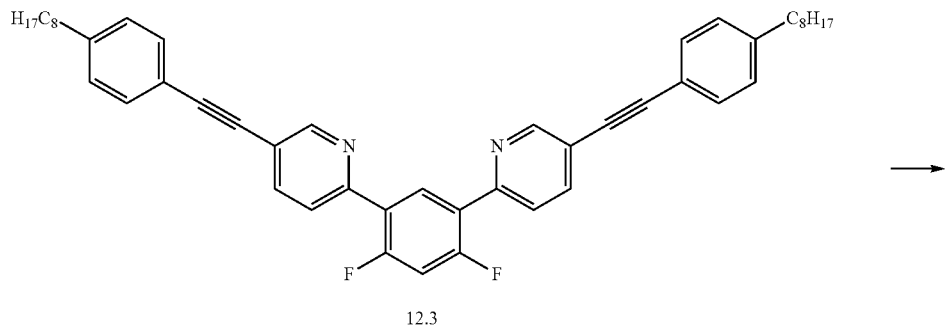

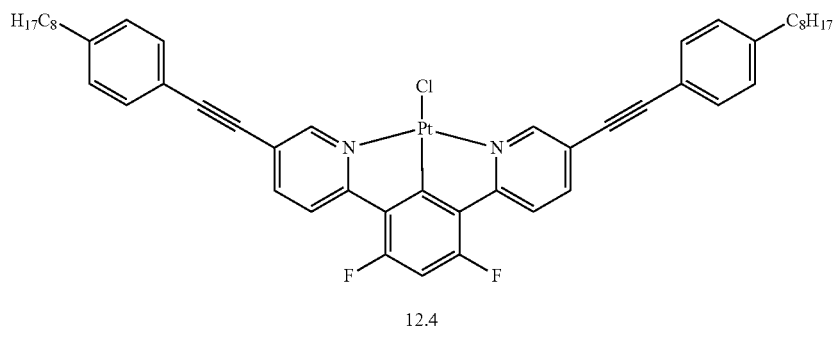

12.4

| 12.1 4,6-difluorobenzene-1,3-diboronic acid dipinacol ester | 12.2 4,6-difluoro-1,3-di(5-bromo-2-pyridyl)benzene |

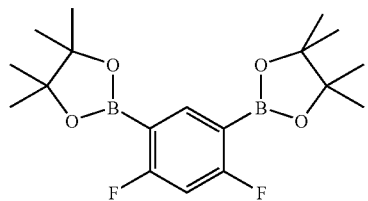

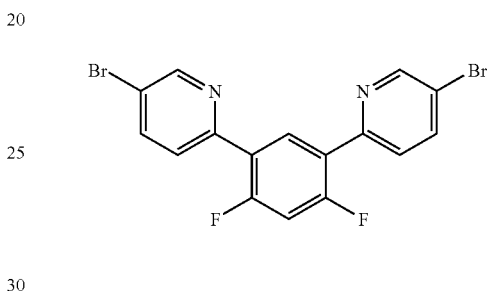

A mixture of 1,5-dibromo-2,4-difluorobenzene (2.72 g, 10 mmol), bispinacolatodiboron (6.6 g, 22 mmol), potassium acetate (4.9 g, 50 mmol), [PdCl$_2$(PPh$_3$)$_2$] and dry DMSO (30 cm$^3$) was degassed by bubbling argon through the mixture for 10 min. The reaction mixture was stirred at 80° C. for 10 h and filtered. The solid on the filter was washed with chloroform (2×50 cm$^3$). The filtrate was washed with water (3×50 cm$^3$). Organic layer was dried under MgSO$_4$ and the solvent was removed under reduced pressure. The residue was dissolved in hot petrol ether (50 cm$^3$) and filtered. The filtrate was evaporated to dryness and the product was purified by column chromatography (silica gel, petrol ether/ethyl acetate, 10/1) to give the title product as colourless solid. Yield 2.6 g, 71%. $\delta_H$ (270 MHz; CDCl$_3$; solvent): 1.34 (24H, s, 8×CH$_3$), 6.71 (1H, t, J 9.8, 5-H), 8.11 (1H, t, J 7.5, 2-H).

A mixture of 2-bromo-5-iodopyridine (6.81 g, 24 mmol), 4,6-difluorobenzene-1,3-diboronic acid dipinacol ester 12.1 (3.66 g, 10 mmol), K$_3$PO$_4$ (6.36 g, 30 mmol) and dry DMF (150 cm$^3$) was degassed by bubbling argon through the mixture for 10 minutes. [Pd(PPh$_3$)$_4$] (693 mg, 0.6 mmol) was added and the mixture was degassed for additional 15 minutes. The reaction mixture was then stirred at 100° C. for 14 hours under argon atmosphere. The solvent was removed under reduced pressure. The residue was treated with methanol (100 cm$^3$) and filtered. The solid was placed in a beaker and stirred with water (100 cm$^3$) for 5 min, filtered, washed with water (50 cm$^3$) and methanol (20 cm$^3$). The solid was then heated to reflux with methanol (100 cm$^3$) cooled to room temperature and filtered to give the titled product. Yield 2.95 g 69%

Example 12.3

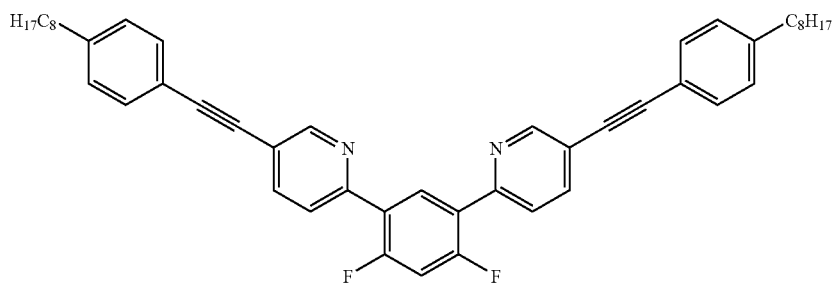

A mixture of dibromo compound 12.2 (190 mg, 0.45 mmol), CuI (0.15 mmol=29 mg), 4-octyl-1-ethynylbenzene (290 mg, 1.35 mmol), dry triethylamine (30 cm$^3$) and dry DMF (30 cm$^3$) was degassed by bubbling argon through the mixture for 15 min. Catalyst [Pd(PPh$_3$)$_4$] (5% mol for every Br 0.045 mol=51 mg) was added and the reaction mixture was heated under reflux for 2 days. The most of the solvent was removed by rotary evaporation. The residue was triturated with ethanol and the precipitated solid was filtered off, washed with ethanol (5 cm$^3$), water (5 cm$^3$) and again ethanol (5 cm$^3$). The solid from the filter was dissolved in chloroform (20 cm$^3$) and filtered through a microfilter. The filtrate was evaporated to dryness and the residue was crystallised from acetone to give colourless crystalline solid. Yield 180 mg, 58%.%. $\delta_H$ (400 MHz; CDCl$_3$): 0.81 (6H, t, J 6.9), 1.1-1.3 (20H, m), 1.55 (4H, q, J 6.6), 2.56 (4H, t, J 7.7), 6.98 (1H, t, J 10.6), 7.12 (4H, AA'XX', J 9.0), 7.46 (4H, AA'XX', J 9.0), 7.72 (2H, br, d, J 8.6), 8.68 (t, 1H, J 9.2), 7.84 (2H, dd, J 8.3, 2.1), 8.78 (2H, dd, J 2.2, 0.7).

Example 12.4

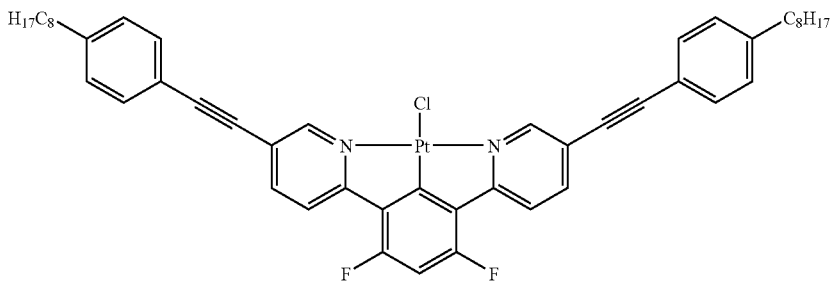

A mixture of the ligand (110 mg, 0.159 mmol), K$_2$[PtCl$_4$] (65 mg, 0.159 mmol) and acetic acid was heated under reflux for 3 days. The solvent was removed under reduced pressure, the residue was purified by column chromatography(silica gel, DCM) to give the complex. Yield 180 mg, 62%. $\delta_H$ (400 MHz; CDCl$_3$): 0.81 (6H, t, J 6.9), 1.1-1.3 (20H, m), 1.55 (4H, q, J 6.6), 2.56 (4H, t, J 7.7), 6.52 (1H, t, J 10.6), 7.10 (4H, AA'XX', J 9.0), 7.40 (4H, AA'XX', J 9.0), 7.68 (2H, br, d, J 8.4), 7.87 (2H, dd, J 8.3, 2.1), 9.18 (2H, d, J 2.0, $^3J_{HPt}$ 38.1).

Examples 13 to 19

The following compounds were prepared by analogous methods to example 7

Example 13

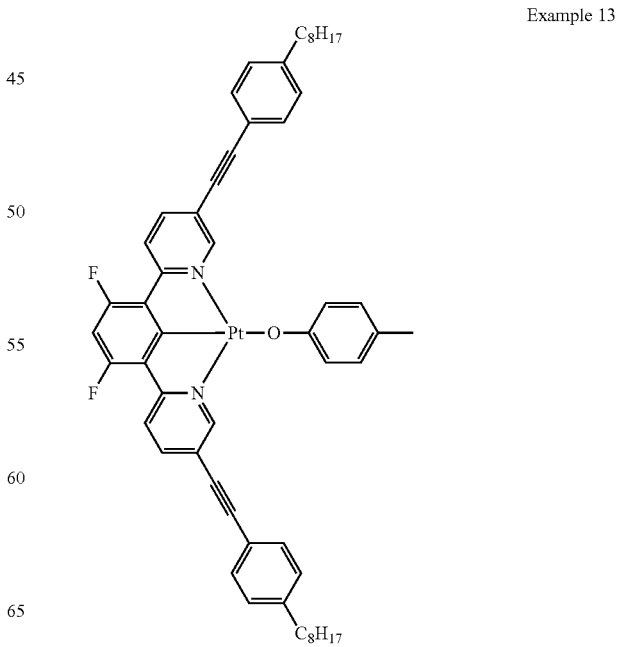

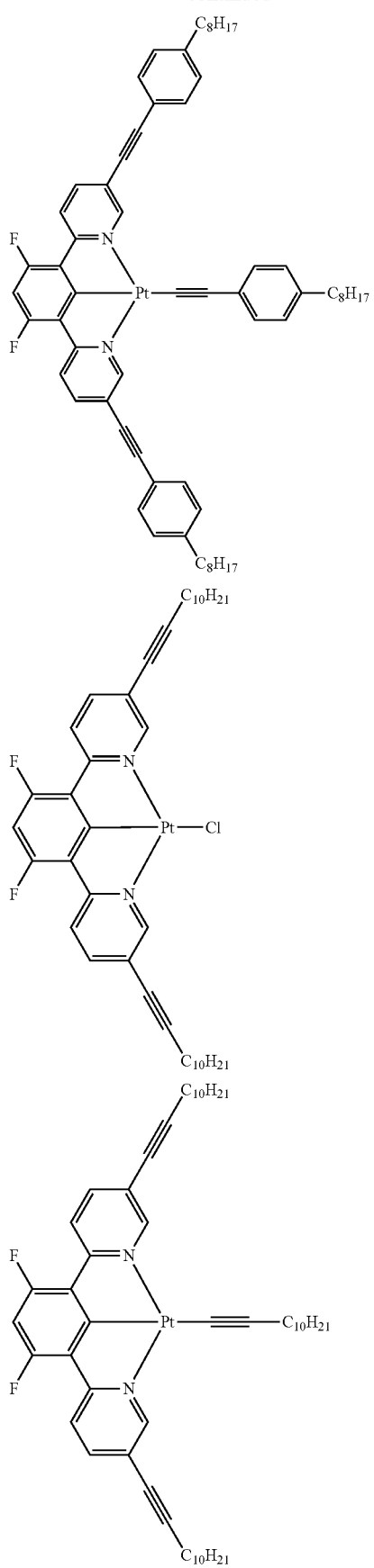
Example 14
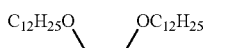
Example 15
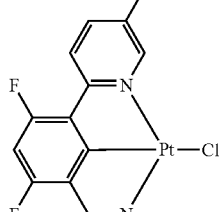
Example 16
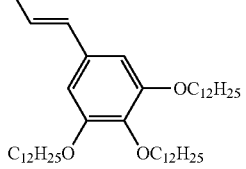
Example 17
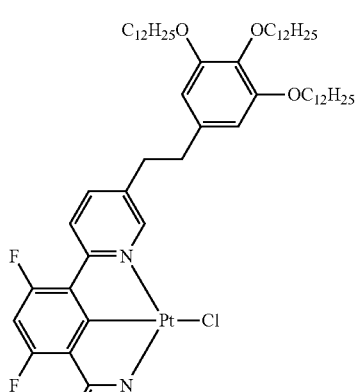
Example 18
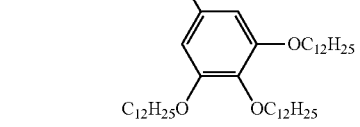
Example 19
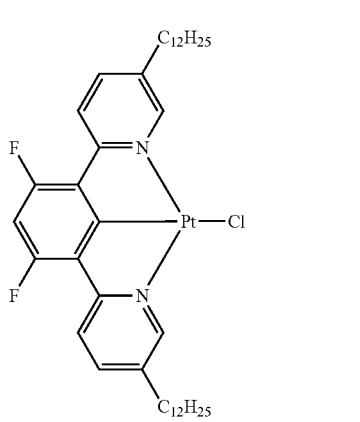

Example 20

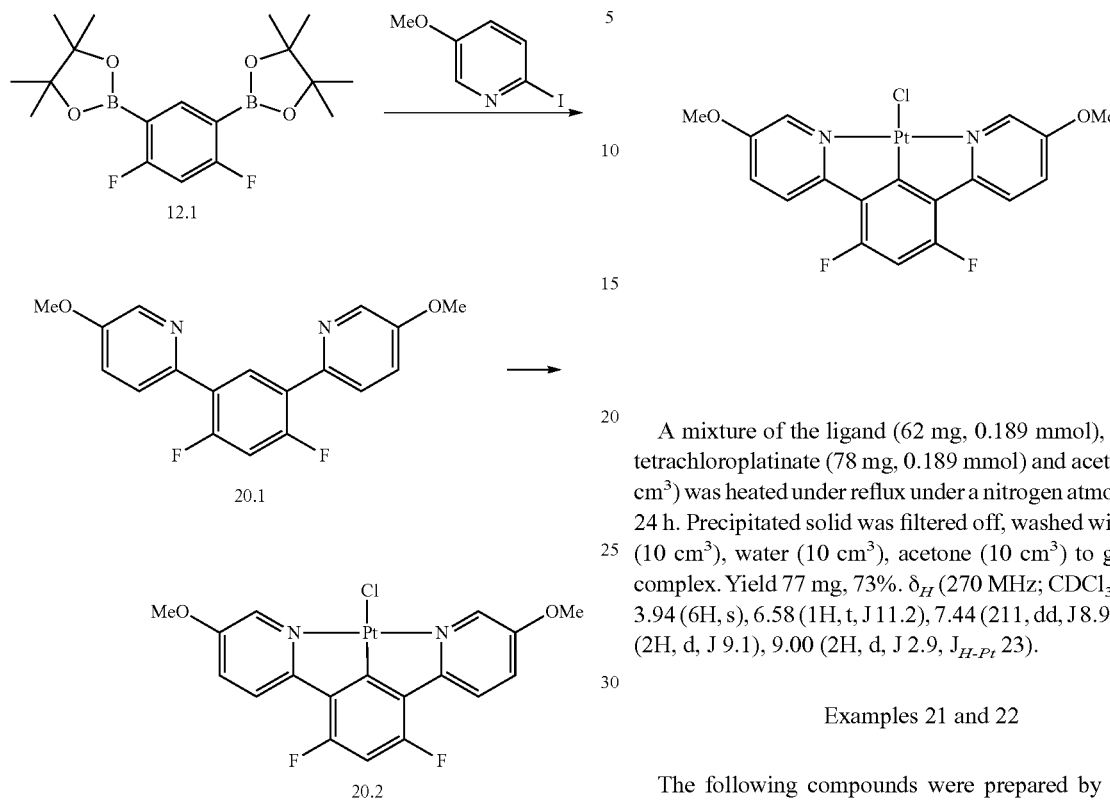

Example 20.1

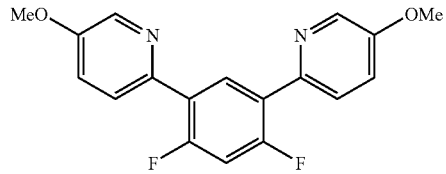

A mixture of 2-bromo-5-methoxypyridine (1 g, 5.3 mmol), 4,6-difluorobenzene-1,3-diboronic acid dipinacol ester (811 mg, 2.2 mmol), K$_3$PO$_4$ (1.40 g, 6.6 mmol) and dry DMF (50 cm$^3$) was degassed by bubbling argon through the mixture for 10 minutes. Pd(PPh$_3$)$_4$ (152 mg, 0.132 mmol) was added and the mixture was degassed for additional 15 minutes. The reaction mixture was then stirred at 100° C. for 14 hours under argon atmosphere. The solvent was removed under reduced pressure and the product is purified by column chromatography (silica gel, ethyl acetate). Yield 550 mg, 45%. δ$_H$ (270 MHz; CDCl$_3$; solvent): 3.89 (6H, s), 6.98 (1H, t, J 10.7), 7.26 (2H, dd, J 8.7, 2.3), 7.70 (2H, d, J 8.6), 8.40 (2H, d, J 2.6), 8.49 (1H, t, J 9.1).

Example 20.2

A mixture of the ligand (62 mg, 0.189 mmol), potassium tetrachloroplatinate (78 mg, 0.189 mmol) and acetic acid (25 cm$^3$) was heated under reflux under a nitrogen atmosphere for 24 h. Precipitated solid was filtered off, washed with acetone (10 cm$^3$), water (10 cm$^3$), acetone (10 cm$^3$) to give the Pt complex. Yield 77 mg, 73%. δ$_H$ (270 MHz; CDCl$_3$; solvent): 3.94 (6H, s), 6.58 (1H, t, J 11.2), 7.44 (2H, dd, J 8.9, 2.8), 7.73 (2H, d, J 9.1), 9.00 (2H, d, J 2.9, J$_{H-Pt}$ 23).

Examples 21 and 22

The following compounds were prepared by analogous methods to example 20

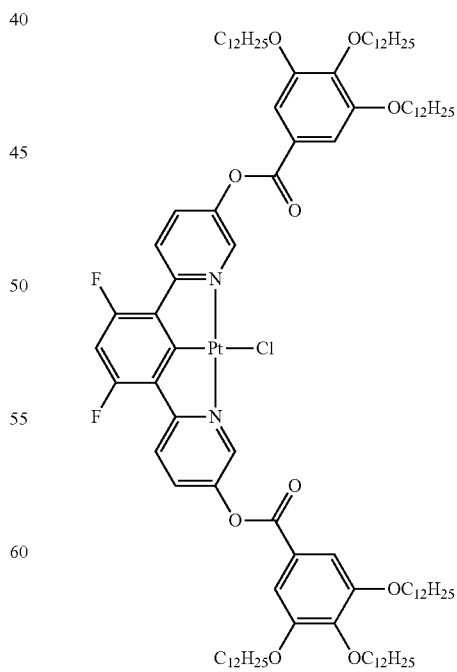

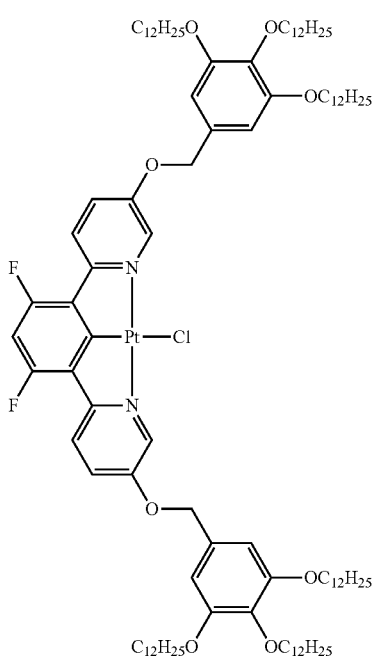

Example 23

1-[5-(3,4,5-trimethoxyphenyl)-3,4-cyclopentenopyridine-2-yl]-3-(5-methylpyridine-2-yl)benzene

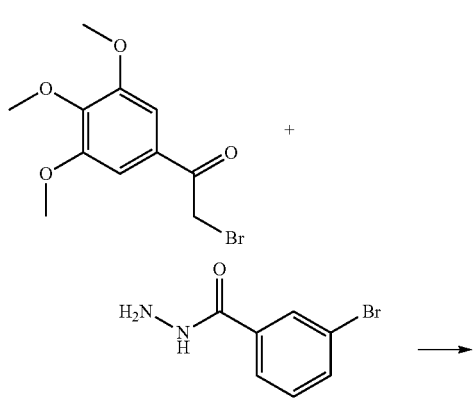

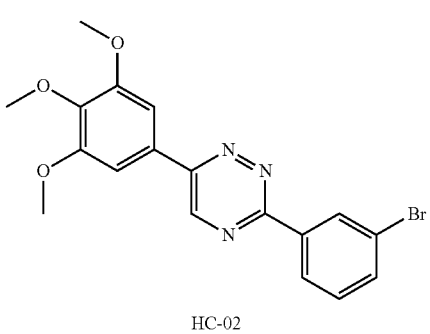

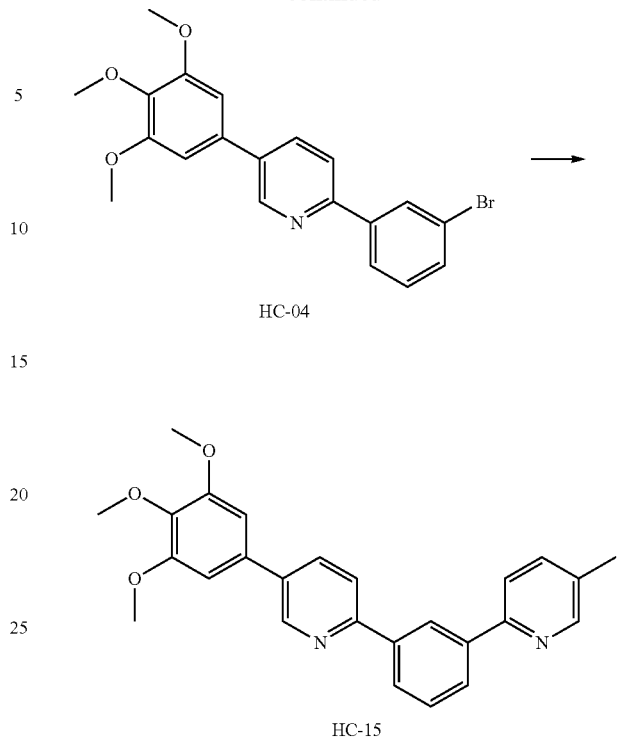

23.1 3-(3-bromophenyl)-6-(3,4,5-trimethoxyphenyl)-1,2,4-triazine

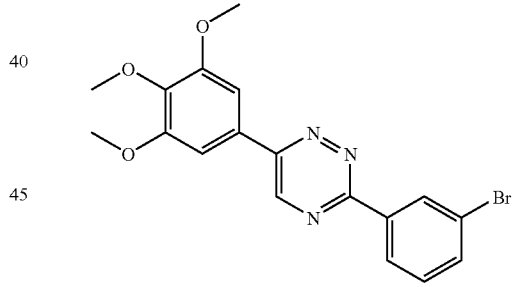

A mixture of 2-bromo-3',4',5'-trimethoxyacetophenone (2.9 g, 10 mmol), 3-bromobenzoyc acid hydrazide (4.3 g, 20 mmol), sodium acetate (1.0 g, 12 mmol), ethanol (30 ml) and acetic acid (10 ml) was heated under reflux for 12 h. The reaction mixture was allowed to cool to room temperature and the precipitated solid was filtered off, washed with ethanol and dried. The product was used in the next step without further purification. Yield 1.8 g, 45%. $\delta_H$ (400 MHz; CDCl$_3$): 2.36 (3H, s), 3.98 (6H, s), 7.39 (2H, s), 7.42 (1H, t, J 8.0), 7.66 (1H, ddd, J 8.0, 2.0, 1.0), 8.50 (1H, ddd, J 8.0, 2.0, 1.0), 8.71 (1H, t, J 2.0), 9.01 (1H, s); $\delta_C$ (CDCl$_3$): 56.37, 61.03, 103.87, 123.13, 126.49, 128.12, 130.43, 131.02, 134.46, 136.52, 140.84, 146.18, 154.02, 154.81, 160.90

23.2 2-(3-bromophenyl)-5-(3,4,5-trimethoxyphenyl)pyridine

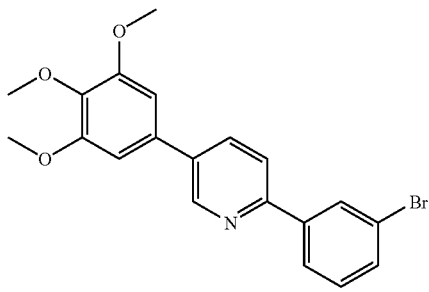

An autoclave equipped with a stirring bar was charged with the triazine 23.1 (1 g, 2.5 mmol), xylene (30 cm³) and norbornadiene (2.3 g, 25 mmol). The autoclave was sealed, placed in oil bath and heated at 200° C. (bath) for 24 h. The reaction mixture was filtered through a small pad of silica gel while hot; the silica gel was washed with DCM (50 cm³). All filtrates were combined and the solvent was removed under reduced pressure. The product was purified by column chromatography (silica gel, petrol ether/ethyl acetate, 1/1) to give the title compound. Yield 2.6 g, 71%. Yield 288 mg, 72%; $\delta_H$ (400 MHz; CDCl₃): 3.84 (3H, s), 3.88 (6H, s), 6.73 (2H, s), 7.29 (1H, t, J 8.0), 7.48 (1H, ddd, J 8.0, 2.0, 1.0), 7.69 (1H, dd, J 8.3, 0.8), 7.85 (1H, dd, J 8.3, 2.4), 7.89 (1H, ddd, J 8.0, 2.0, 1.0), 8.15 (1H, t, J 2.0), 8.82 (1H, dd, J 2.4, 0.8).

23.3 1-[5-(3,4,5-trimethoxyphenyl)-3,4-cyclopentenopyridine-2-yl]-3-(5-methylpyridine-2-yl)benzene A mixture of the bromo derivative 23.2 (220 mg, 0.5 mmol), 5-methyl-2-tri-n-butylstannylpyridine (287 mg, 0.75 mmol), lithium chloride (424 mg, 10 mol), bis(triphenylphosphine)palladium dichloride (36 mg, 0.05 mmol) and toluene (15 cm³) was degassed by bubbling argon through the mixture for 15 minutes. The reaction mixture was heated under reflux for 24 h. The solvent was removed by rotary evaporation under reduced pressure. The product was purified by column chromatography (silica gel, DCM/ethyl acetate/hexane, 1/1/1) to give the title compound. Yield 116 mg, 51%. $\delta_H$ (270 MHz; CDCl₃): 2.39 (3H, s), 3.90 (3H, s), 3.95 (6H, s), 6.81 (2H, s), 7.59 (2H, m), 7.74 (1H, br, d, J 8.1), 7.91 (2H, br, s), 8.0-8.1 (2H, m), 8.54 (1H, br, s), 8.64 (1H, br, s), 8.91 (1H, br, s).

Example 23 was prepared using this approach along with chemistry hereinbefore described.

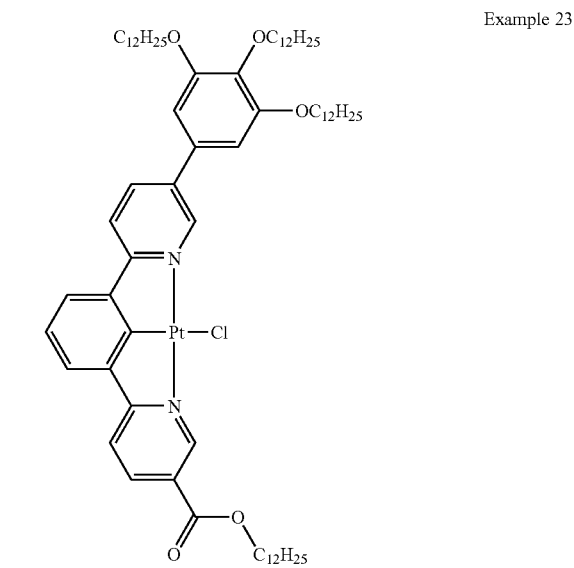

Example 23

Figure Legends:

FIG. 1

Example 2, n=6

Large, well-developed domains were obtained by cooling slowly from the isotropic melt into the LC phase and then rapidly to room temperature. The emission spectrum (alongside) reveals structured, monomer emission at 575 nm and 624 nm. FIG. 1(b) shows the photomicrograph obtained when the same complex is cooled rapidly directly from the isotropic melt. Here the domains are very small, which means that there is a high concentration of (isotropic) grain boundaries; no monomer emission is observed, rather excimer-like emission (690 nm), which normally characterises these materials. In the columnar phase, X-ray evidence suggests that the complexes are constrained into an antiparallel arrangement in which they behave independently (monomers). However, in FIG. 1b the sample is dominated by isotropic grain boundaries in which the complexes are free to adopt excimer-like structures from which longer-wavelength emission is observed. Thus, organisation into the LC phase offers a degree a control and access to a monomer-like emission regime, very different from the excimer-like emission that normally characterizes these materials.

FIG. 2

FIG. 2 shows spectra from example 2, n=6 spin coated onto a glass substrate. As prepared, the film shows only excimer-like emission (λ=660 nm). However, after heating to 110° C. followed by cooling to room temperature, there is a drastic change in emission colour from the red of the excimer to the yellow of the simultaneous emission from monomer and excimer. However, the red emission of the excimer is recovered if the film is now subjected to mechanical disturbance such as rubbing. A further heat-cool cycle re-establishes monomer emission. Thus, the emission characteristics can readily be further controlled and, more than that, can be influenced by an external, mechanical stimulus, with the original state being recovered by thermal cycling. One possible application of this could be to print the OLED onto a flexible substrate and use it to detect weld failures. Simultaneous emission from monomer and excimer covers a broad spectral region and if shifted a little to the blue would give white emission, of interest for lighting applications.

REFERENCES i R. C. Evans, P. Douglas, C. J. Winscom, *Coord. Chem. Rev.*, 2006, 250, 2093.

ii D. Adam, P. Schumacher, J. Simmerer, L. Haeussling, K. Siemensmeyer, K. H. Etzbach, H. Ringsdorf, D. Haarer, *Nature*, 1994, 371, 141.

iii S. J. Farley, D. L. Rochester, A. L. Thompson, J. A. K. Howard, J. A. G. Williams, *Inorg. Chem.*, 2005, 44, 9690.

iv B. B. Dey, *J. Chem. Soc.*, 1914, 105, 1039.

v G. B. Bennett, R. B. Mason, L. J. Alden, J. B. Roach, *J. Med. Chem.*, 1978, 21, 623.

vi Pyridinium hydrochloride is a classical reagent for cleavage of aryl methyl ethers at 200-220° C. avoiding strongly acidic or basic conditions: V. Prey, *Chem. Ber.*, 1942, 75B, 350.

The invention claimed is:

1. A metal-ligand complex comprising a complex of formula I:

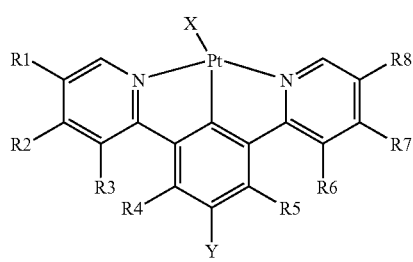

I in which $R^1$ and $R^8$, which may be the same or different, are each a group of formula II;

$$-Z-R^{12}$$  II

Z is a sigma-bond, $-C=C-$, $-C\equiv C-$, $-(CH_2)_x-$, $-COO-$, $-OC(=O)-$, $-CH=N-$, $-N=CH-$, $-C(=O)NH-$, $-NHC(=O)-$, $-(CH_2)_qO-$, $-O-(CH_2)_w-$ or $-OC(=O)X^1R^{14}-$;

$R^{12}$ is alkyl C1 to 18 or a group of formula VIII;

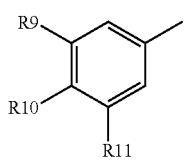

VIII $R^2$, $R^3$, $R^6$ and $R^7$, which may be the same or different, are each hydrogen or together the pair of $R^2$ and $R^3$ or $R^6$ and $R^7$, form a $-(CH_2)_m-$ ring;

$R^4$ and $R^5$, which may be the same or different, are each hydrogen or halogen;

X is a phenate, a thiolate, an acetylide, a phenyl, an alkyl, vinyl, each of which may optionally be substituted by alkyl C1 to 30 or X is a halide;

$X^1$ is C5 or C6 cycloalkyl;

Y is hydrogen, hydroxy, halogen, alkyl C1 to 6, haloalkyl C1 to 6, alkoxy C1 to 6, $-COOR^{13}$, cyano or isothiocyanate;

$R^9$ and $R^{11}$, which may be the same or different, are each hydrogen or $-OC_nH_{2n+1}$;

$R^{10}$ is hydrogen, $-OC_nH_{2y+1}$ $R^{13}$ is hydrogen or alkyl C1 to 18;

$R^{14}$ is alkyl C1 to 12;

m is an integer from 3 to 8;

n and y, which may be the same or different, are each an integer from 1 to 30; and x, q and w, which may be the same or different, are each an integer from 1 to 12.

2. A metal-ligand complex according to claim 1 wherein the platinum in the complex is $Pt^{II}$.

3. A metal-ligand complex according to claim 1 wherein each of $R^2$, $R^3$, $R^6$ and $R^7$ is hydrogen.

4. A metal-ligand complex according to claim 1 wherein $R^4$ and $R^5$ are each hydrogen.

5. A metal-ligand complex according to claim 1 wherein X is Cl.

6. A metal-ligand complex according to claim 1 wherein the complex is selected from the group consisting of:
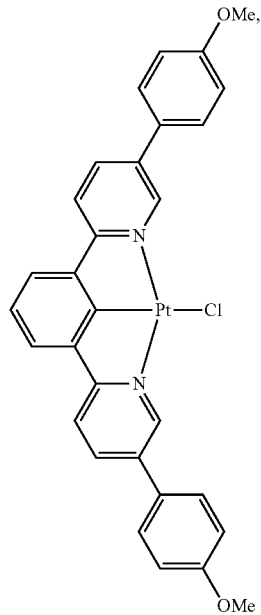
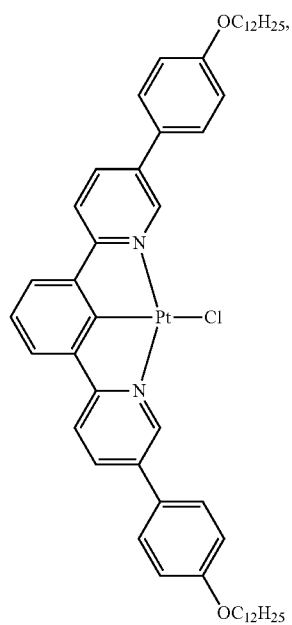

-continued
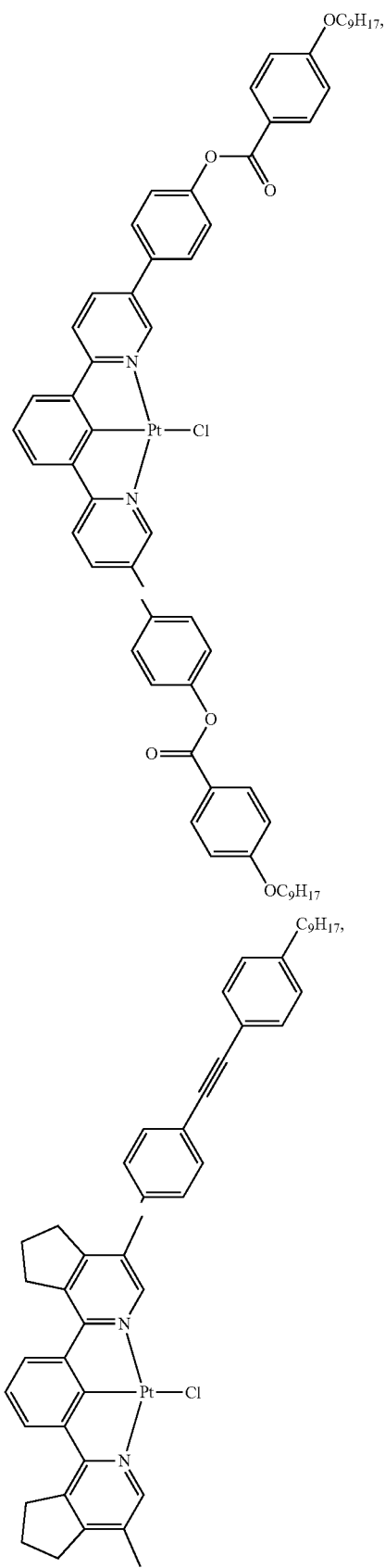

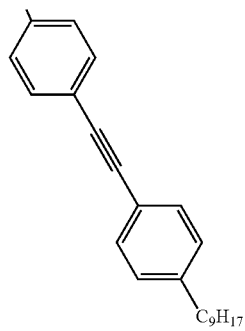
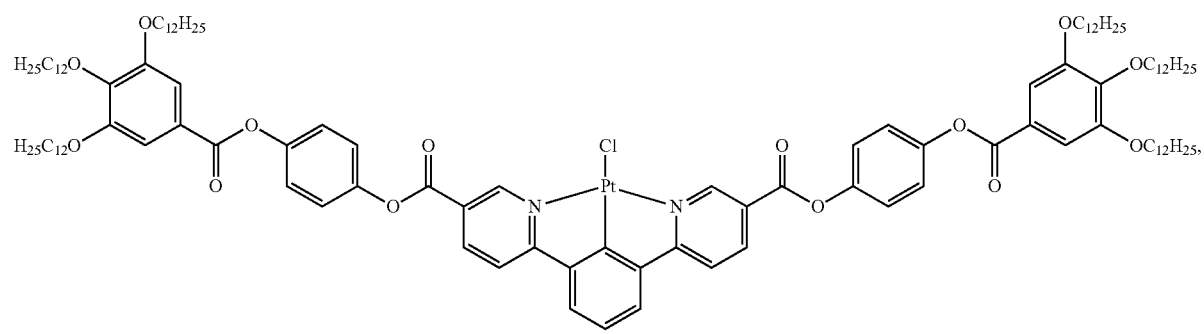
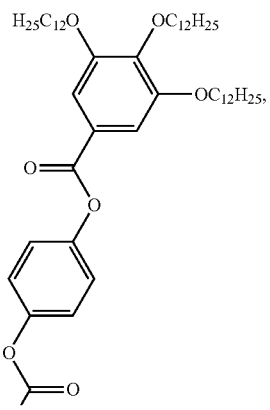
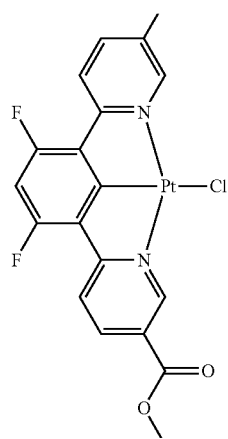

-continued
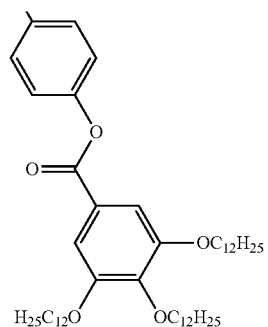
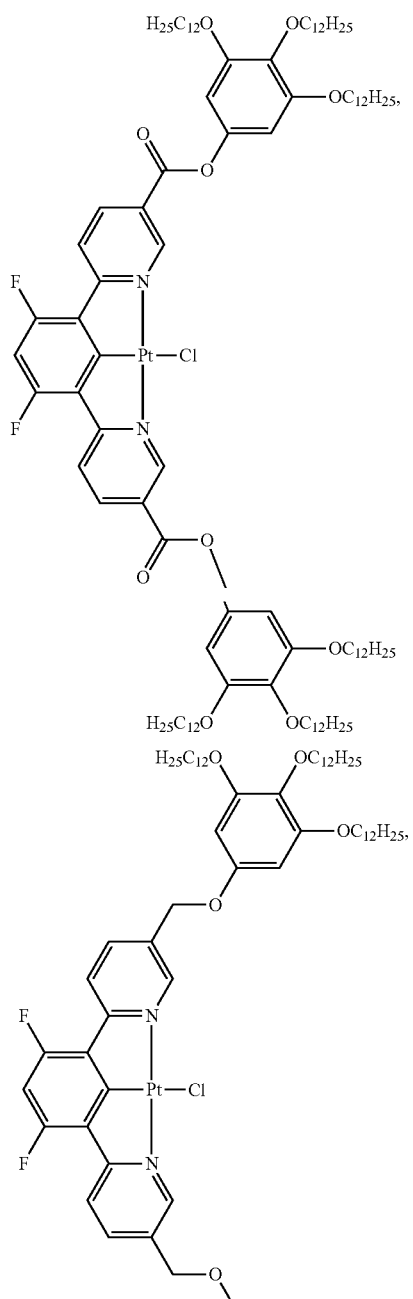

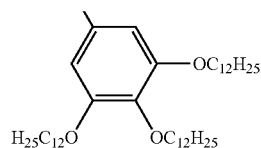
-continued
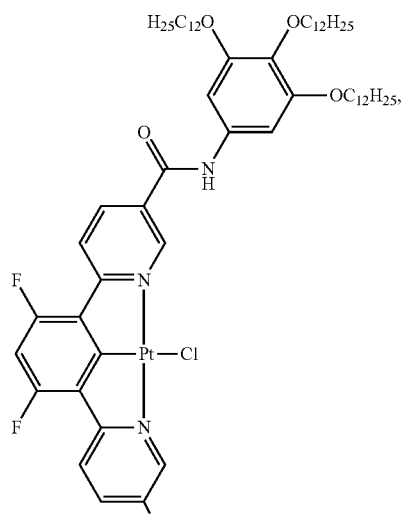
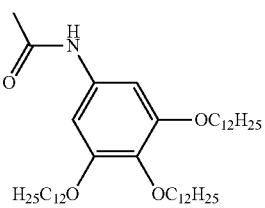
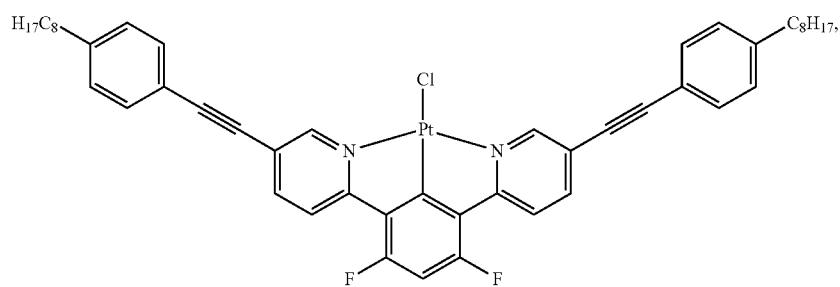

-continued
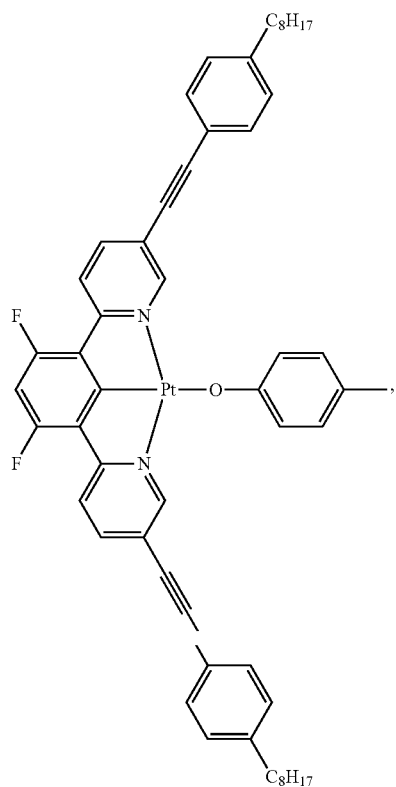
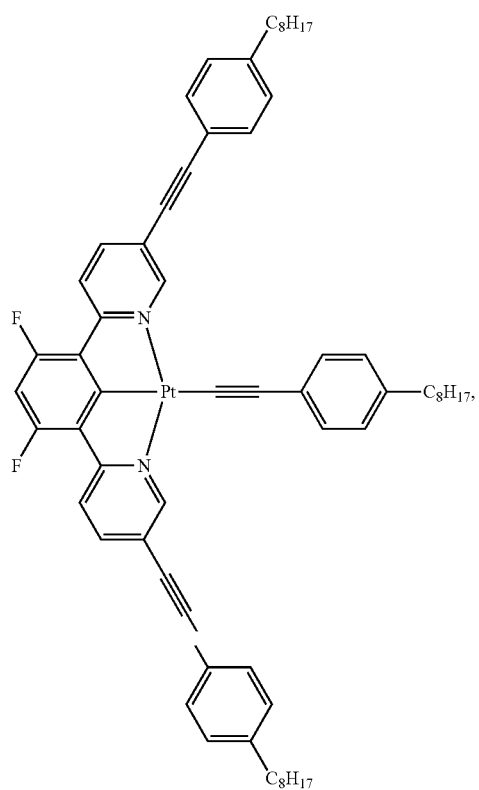

-continued
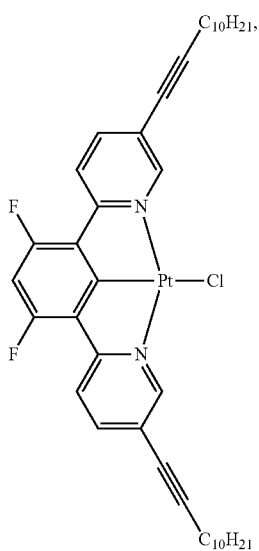
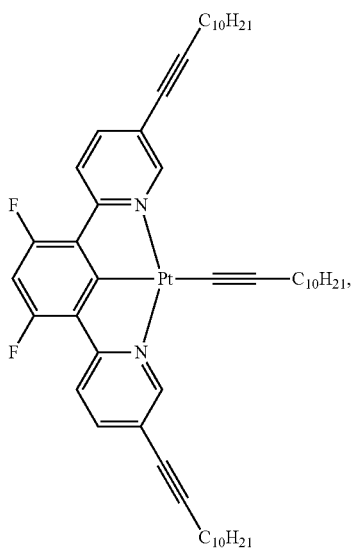
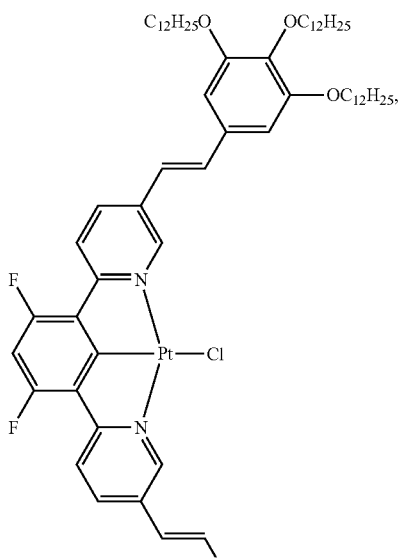

-continued
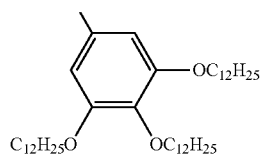
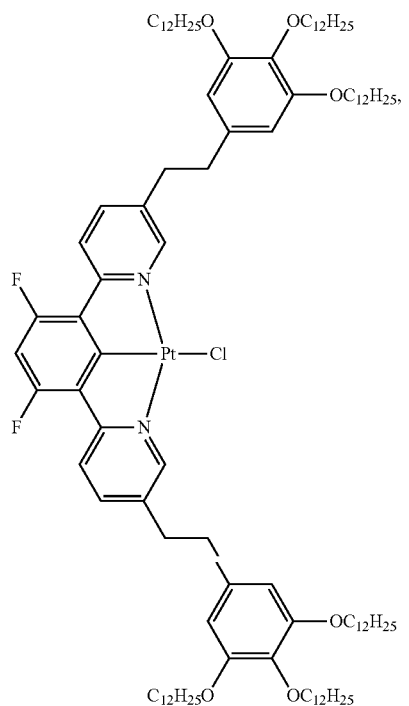
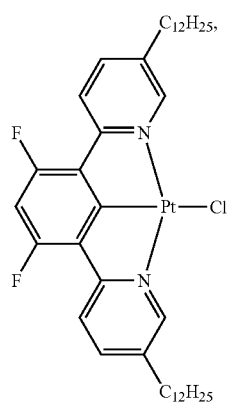
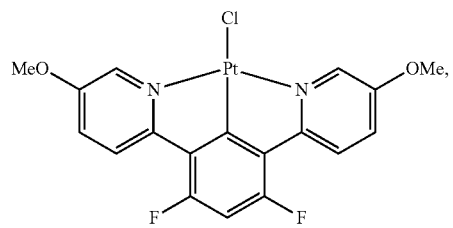

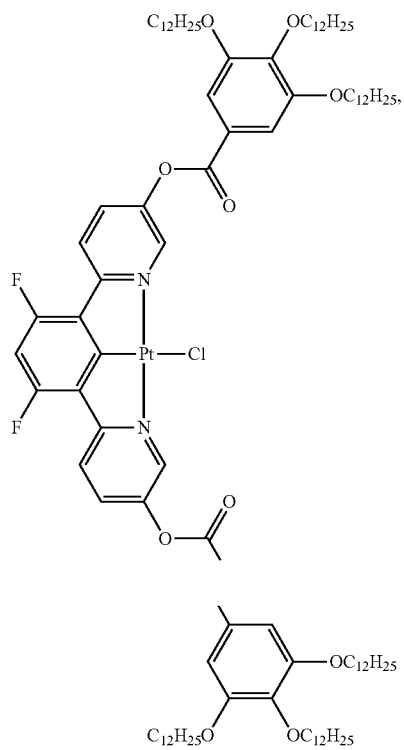
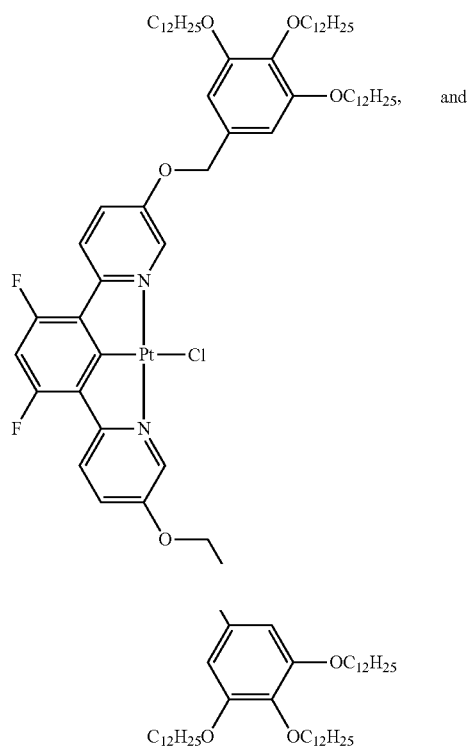

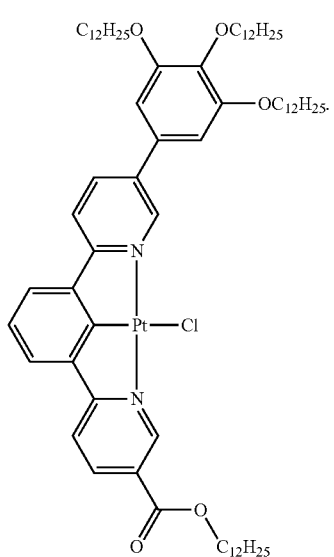
7. A material comprising an organo-platinum according to claim 1 with liquid crystal properties.
* * * * *